(12) United States Patent
Brown

(10) Patent No.: US 6,794,380 B2
(45) Date of Patent: Sep. 21, 2004

(54) AMIDE DERIVATIVES

(75) Inventor: Dearg S Brown, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 43 days.

(21) Appl. No.: 10/353,127

(22) Filed: Jan. 29, 2003

(65) Prior Publication Data

US 2003/0186966 A1 Oct. 2, 2003

Related U.S. Application Data

(62) Division of application No. 09/936,698, filed as application No. PCT/GB00/00914 on Mar. 13, 2000, now Pat. No. 6,548,514.

(30) Foreign Application Priority Data

Mar. 17, 1999 (GB) ............................................. 9906277
Feb. 3, 2000 (GB) ............................................. 0002472

(51) Int. Cl.$^7$ ...................... A61K 31/33; A61K 31/435; C07D 213/02; C07D 241/00; C07D 295/00
(52) U.S. Cl. .................... 514/183; 514/277; 514/252.1; 546/262; 546/264; 546/266; 546/267; 544/336; 544/106; 544/224; 544/358
(58) Field of Search ................................. 514/183, 277, 514/252.1; 546/262, 264, 266, 267; 544/336, 106, 224, 358

(56) References Cited

U.S. PATENT DOCUMENTS

| | | |
|---|---|---|
| 6,432,949 B1 | 8/2002 | Brown et al. |
| 6,455,520 B1 | 9/2002 | Brown et al. |
| 6,465,455 B1 | 10/2002 | Brown et al. |
| 6,498,274 B1 | 12/2002 | Brown et al. |

FOREIGN PATENT DOCUMENTS

| | | |
|---|---|---|
| DE | 522 788 | 3/1931 |
| EP | 0 849 256 A1 | 6/1998 |
| WO | WO 98/22103 | 5/1998 |
| WO | 98/22103 | 5/1998 |
| WO | 99/15164 | 4/1999 |
| WO | WO 99/15164 | 4/1999 |
| WO | 99/59959 | 11/1999 |
| WO | 00/07980 | 2/2000 |
| WO | 00/07991 | 2/2000 |
| WO | 00/20402 | 4/2000 |
| WO | 00/55153 | 9/2000 |
| WO | 00/56738 | 9/2000 |
| WO | 01/27089 | 4/2001 |

OTHER PUBLICATIONS

Denny et al,"Potential antitumor Agts . . . Heterocycles", J. Med. Chem., 22/2, 134–150(1979).*
Denny et al., "Potential Antitumour Agents. 29. Quantitative Structure–Activity Relationships for the Antileukemic Bisquaternary Ammonium Heterocycles", Journal of Medicinal Chemistry, Feb. 1979, vol. 22, No. 2, pp. 134–150.
Hanson, "Review—Pulmonary–Allergy, Dermatological, Gastrointestinal & Arthritis—Inhibitors of p38 kinase", Exp. Opin. Ther. Patents, 1997, XP–002086152, pp.729–733.

* cited by examiner

*Primary Examiner*—Richard L. Raymond
*Assistant Examiner*—Sudhaker B. Patel
(74) *Attorney, Agent, or Firm*—Morgan, Lewis & Bockius LLP

(57) ABSTRACT

The invention concerns amide derivatives of the Formula I

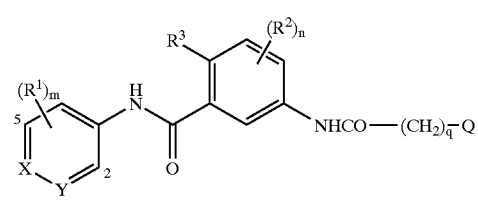

wherein X is CH or N; Y is CH or N; m is 0–3; $R^1$ is a group such as hydroxy, halogeno, trifluoromethyl, cyano, mercapto, nitro, amino, carboxy and carbamoyl; n is 0–3; $R^2$ is a group such as hydroxy, halogeno, trifluoromethyl, cyano, mercapto, nitro, amino, carboxy and (1–6C)alkoxycarbonyl; $R^3$ is hydrogen, halogeno, (1–6C)alkyl or (1–6C)alkoxy;
q is 0–4; and Q is a group such as aryl, aryloxy, aryl-(1–6C)alkoxy, arylamino, N-(1–6C)alkyl-arylamino and aryl-(1–6C)alkylamino; or pharmaceutically-acceptable salts or in-vivo-cleavable esters thereof; processes for their preparation, pharmaceutical compositions containing them and their use in the treatment of diseases or medical conditions mediated by cytokines.

17 Claims, No Drawings

AMIDE DERIVATIVES

This application is a Division of U.S. application Ser. No. 09/936,698, filed Sep. 17, 2001, now U.S. Pat. No. 6,548,514, which is a 371 of PCT/GB00/00914, filed Mar. 13, 2000, which claims priority to United Kingdom applications GB 9906277.0 filed Mar. 17, 1999 & GB 0002472.9, filed Feb. 3, 2000.

This invention concerns certain amide derivatives which are useful as inhibitors of cytokine mediated disease. The invention also concerns processes for the manufacture of the amide derivatives of the invention, pharmaceutical compositions containing them and their use in therapeutic methods, for example by virtue of inhibition of cytokine mediated disease.

The amide derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the compounds of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune systems, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis, adult respiratory distress syndrome and chronic obstructive pulmonary disease), and in the production and development of various cardiovascular and cerebrovascular disorders such as congestive heart failure, myocardial infarction, the formation of atherosclerotic plaques, hypertension, platelet aggregation, angina, stroke, Alzheimer's disease, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoperosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

Evidence of the central role played by TNFα in the cell signalling cascade which gives rise to rheumatoid arthritis is provided by the efficacy in clinical studies of antibodies of TNFα (*The Lancet*, 1994, 344, 1125 and *British Journal of Rheumatology*, 1995, 34, 334).

Thus cytokines such as TNFα and IL-1 are believed to be important mediators of a considerable rankle of diseases and medical conditions. Accordingly it is expected that inhibition of the production of and/or effects of these cytokines will be of benefit in the prophylaxis, control or treatment of such diseases and medical conditions.

Without wishing to imply that the compounds disclosed in the present invention possess pharmacological activity only by virtue of an effect on a single biological process, it is believed that the compounds inhibit the effects of cytokines by virtue of inhibition of the enzyme p38 kinase. p38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFα and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed by G J Hanson in *Expert Opinions on Therapeutic Patents*, 1997, 7, 729–733. p38 kinase is known to exist in isoforms identified as p38α and p38β.

The compounds disclosed in the present invention are inhibitors of the production of cytokines such as TNF, in particular of TNFα, and various interleukins, in particular IL-1.

According to a first aspect of the present invention there is provided a compound of the Formula I

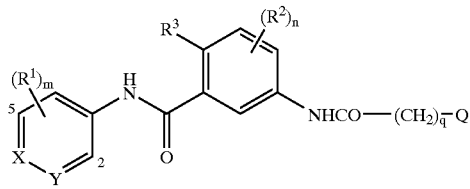

wherein X is CH or N;
Y is CH or N;
m is 0, 2, or 3;
R¹ is hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino or di-[(1–6C)alkyl]amino-(2–6C)alkanoylamino,
or R¹ is aryl, aryl-(1–6C)alkyl, aryl-(1–6C)alkoxy, aryloxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C) alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heteroaryl-(1–6C)alkoxy-(1–6C)alkyl, heteroaryl-(1–6C)alkylamino-(1–6C)alkyl, N-(1–6C)alkyl-heteroaryl-(1–6C)alkylamino-(1–6C)alkyl, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclysulphonylamino, N-heterocyclylsulphamoyl, heterocyclyl-(2–6C)alkanoylamino, heterocyclyl-(1–6C)alkoxy-(1–6C)alkyl, heterocyclyl-(1–6C)alkylamino-(1–6C)alkyl or N-(1–6C)alkyl-heterocyclyl-(1–6C)alkylamino-(1–6C)alkyl,
or (R¹)ₘ is a (1–3C)alkylenedioxy group,
and wherein any of the R¹ substituents defined hereinbefore which comprises a CH₂ group which is attached to 2 carbon atoms or a CH₃ group which is attached to a carbon atom may optionally bear on each said CH₂ or CH₃ group a substituent selected from hydroxy, amino, (1–6C)alkoxy, (1–6C)alkylamino, di-[(1–6C)alkyl]amino and heterocyclyl, and wherein any aryl, heteroaryl or heterocyclyl group in a R¹ substituent may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl]carbamoyl, (2–6C)alkanoyl, amino, (1–6C)alkylamino, di-[(1–6C)alkyl]amino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl,
n is 0, 1, 2 or 3;
R² is hydroxy, halogeno, trifluoromethyl, cyano, mercapto, nitro, amino, carboxy, (1–6C)alkoxycarbonyl, (1–6C)alkyl, (2–6C)alkenyl, (2–6C)alkynyl, (1–6C)alkoxy, (1–6C)alkylamino or di-[(1–6C)alkyl]amino;
R³ is hydrogen, halogeno, (1–6C)alkyl or (1–6C)alkoxy;
q is 0, 1, 2, 3 or 4; and
Q is aryl, aryloxy, aryl-(1–6C)alkoxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylcarbamoyl, N-arylsulphamoyl, aryl-(2–6C)alkanoylamino, (3–7C)cycloalkyl, heteroaryl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylcarbamoyl, N-heteroarylsulphamoyl, heteroaryl-(2–6C)alkanoylamino, heterocyclyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylcarbamoyl, N-heterocyclylsulphamoyl or heterocyclyl-(2–6C)alkanoylamino, and Q is optionally substituted with 1, 2 or 3 substituents selected from hydroxy, halogeno, trifluoromethyl, cyano, mercapto, nitro, amino, carboxy, carbamoyl formyl, (1–6C)alkyl, (2–6C)alkenyl, (2–6C)alkynyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)

alkylcarbamoyl, N,N-di-[(1–6C)alkyl]carbamoyl, (2–6C) alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkyl-amino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino, di-[(1–6C)alkyl]amino-(2–6C)alkanoylamino, aryl, aryl-(1–6C)alkyl, aryl-(1–6C)alkoxy, aryloxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heteroaryl-(1–6C)alkoxy-(1–6C)alkyl, heteroaryl-(1–6C)alkylamino-(1–6C)alkyl, N-(1–6C)alkyl-heteroaryl-(1–6C)alkylamino-(1–6C)alkyl, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl, heterocyclyl-(2–6C)alkanoylamino, heterocyclyl-(1–6C)alkoxy-(1–6C)alkyl, heterocyclyl-(1–6C)alkylamino-(1–6C)alkyl and N-(1–6C)alkyl-heterocyclyl-(1–6C)alkylamino-(1–6C)alkyl, or Q is substituted with a (1–3C)alkylenedioxy group, and wherein any of the substituents on Q defined hereinbefore which comprises a CH$_2$ group which is attached to 2 carbon atoms or a CH$_3$ group which is attached to a carbon atom may optionally bear on each said CH$_2$ or CH$_3$ group a substituent selected from hydroxy, amino, (1–6C)alkoxy, (1–6C)alkylamino, di-[(1–6C)alkyl]amino and heterocyclyl, and wherein any aryl, heteroaryl or heterocyclyl group in a substituent on Q may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl]carbamoyl, (2–6C)alkanoyl, amino, (1–6C)alkylamino, di-[(1–6C)alkyl]amino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl; or a pharmaceutically-acceptable salt or in-vivo-cleavable ester thereof.

According to a second aspect of the present invention there is provided a compound of the Formula I wherein each of X, Y, R$^1$, R$^2$, m, n, q and Q have any of the meanings defined hereinbefore and R$^3$ is selected from halogeno and (1–6C)alkyl; or a pharmaceutically-acceptable salt or in-vivo-cleavable ester thereof.

In this specification, the term (1–6C)alkyl includes straight-chain and branched-chain alkyl groups such as propyl, isopropyl and tert-butyl, and (3–6C)cycloalkyl (groups such as cyclopropyl, cyclobutyl, cyclopentyl and cyclohexyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1–6C)alkoxy includes methoxy, ethoxy, cyclopropyloxy and cyclopentyloxy, (1–6C)alkylamino includes methylamino, ethylamino, cyclobutylamino and cyclohexylamino, and di-[(1–6Calkyl]amino includes dimethylamino, diethylamino, N-cyclobutyl-N-methylamino and N-cyclohexyl-N-ethylamino.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry, well known in the art, for example by synthesis from optically active starting materials or by resolution of a racemic form. Similarly, inhibitory properties against TNF may be evaluated using the standard laboratory techniques referred to hereinafter.

Suitable values for the generic radicals referred to above include those set out below.

A suitable value for R$^1$ or Q when it is aryl, for a substituent on Q when it is aryl or for the aryl group within a R$^1$ substituent or a Q group or within a substituent on Q is, for example, phenyl, indenyl, indanyl naphthyl, tetrahydronaphthyl or fluorenyl, preferably phenyl.

A suitable value for R$^1$ or Q when it is heteroaryl, for the heteroaryl group within a R$^1$ substituent or a Q group, for a substituent on Q when it is heteroaryl or for the heteroaryl group within a substituent on Q is, for example, an aromatic 5- or 6-membered monocyclic ring, a 9- or 10-membered bicyclic ring or a 13- or 14-membered tricyclic ring each with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl, naphthyridinyl, carbazolyl, dibenzofuranyl, dibenzothiophenyl, S,S-dioxodibenzothiophenyl, xanthenyl, dibenzo-1,4-dioxinyl, phenoxathiinyl, phenoxazinyl, dibenzothiinyl, phenothiazinyl, thianthrenyl, benzofuropyridyl, pyridoindolyl, acridinyl or phenanthridinyl, preferably furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl, more preferably furyl, thienyl, isoxazolyl, thiazolyl, pyridyl, benzothienyl, benzofurazanyl, quinolyl, carbazolyl, dibenzofuranyl or dibenzothiophenyl.

A suitable value for $R^1$ or Q when it is heterocyclyl, for a substituent on Q when it is heterocyclyl or for the heterocyclyl group within a $R^1$ substituent or a Q group or within a substituent on Q is, for example, a non-aromatic saturated or partially saturated 3- to 10-membered monocyclic or bicyclic ring with up to five heteroatoms selected from oxygen, nitrogen and sulphur, for example oxiranyl, oxetanyl, azetidinyl, tetrahydrofuranyl, tetrahydropyranyl, pyrrolinyl, pyrrolidinyl, 1,1-dioxidoisothiazolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, or, for example, imidazolinyl, imidazolidinyl, pyrazolinyl, pyrazolidinyl, or, for example, benzo derivatives thereof such as 2,3-dihydrobenzofuranyl, 2,3-dihydrobenzothienyl, indolinyl, isoindolinyl, chromanyl and isochromanyl, preferably the heterocyclyl group is pyrrolidin-1-yl, pyrrolidin-2-yl, morpholino, piperidino, piperazin-1-yl or homopiperazin-1-yl.

A suitable value for Q when it is (3–7C)cycloalkyl is, for example, a non-aromatic mono- or bicyclic 3- to 7-membered carbon ring such as cyclopropyl, cyclobutyl, cyclopentyl, cyclohexyl, cycloheptyl or bicyclo[2.2.1]heptyl, preferably cyclobutyl, cyclopentyl, cyclohexyl or cycloheptyl, more preferably cyclohexyl.

Suitable values for various $R^1$, $R^2$ or $R^3$ groups, or for various substituents on Q or on an aryl, heteroaryl or heterocyclyl group within $R^1$ or on an aryl, heteroaryl or heterocyclyl group on a substituent on Q include:

for halogeno: fluoro, chloro, bromo and iodo;
for (1–6C)alkyl): methyl, ethyl, propyl, isopropyl, tert-butyl, cyclobutyl, cyclopentyl and cyclohexyl;
for (2–6C)alkenyl: vinyl and allyl;
for (2–6C)alkynyl: ethynyl and 2-propynyl;
for (1–6C)alkoxy: methoxy, ethoxy, propoxy, isopropoxy, cyclopropyloxy, butoxy, cyclobutyloxy and cyclopentyloxy;
for (1–6C)alkylamino: methylamino, ethylamino, propylamino, cyclobutylamino and cyclohexylamino;
for di-[(1–6C)alkyl]amino: dimethylamino, diethylamino and N-ethyl-N-methylamino;
for (1–6C)alkoxycarbonyl: methoxycarbonyl, ethoxycarbonyl, propoxycarbonyl and tert-butoxycarbonyl;
for N-(1–6C)alkylcarbamoyl: N-methylcarbamoyl, N-ethylcarbamoyl and N-propylcarbamoyl;
for N,N-di-[(1–6C)alkyl]carbamoyl: N,N-dimethylcarbamoyl, N-ethyl-N-methylcarbamoyl and N,N-diethylcarbamoyl;
for (2–6C)alkanoyl: acetyl and propionyl;
for halogeno-(1–6C)alkyl: fluoromethyl, chloromethyl, bromomethyl, difluoromethyl, dichloromethyl, dibromomethyl, 2-fluoroethyl, 2-chloroethyl and 2-bromoethyl;
for hydroxy-(1–6C)alkyl: hydroxymethyl, 2-hydroxyethyl, 1-hydroxyethyl and 3-hydroxypropyl;
for (1–6C)alkoxy-(1–6C)alkyl: methoxymethyl, ethoxymethyl, 1-methoxyethyl, 2-methoxyethyl, 2-ethoxyethyl and 3-methoxypropyl;
for cyano-(1–6C)alkyl: cyanomethyl, 2-cyanoethyl, 1-cyanoethyl and 3-cyanopropyl;
for amino-(1–6C)alkyl: aminomethyl, 2-aminoethyl, 1-aminoethyl and 3-aminopropyl;
for (1–6C)alkylamino-(1–6C)alkyl: methylaminomethyl, ethylaminomethyl, 1-methylaminoethyl, 2-methylaminoethyl, 2-ethylaminoethyl and 3-methylaminopropyl;
for di-[(1–6C)alkyl]amino-(1–6C)alkyl: dimethylaminomethyl, diethylaminomethyl, 1-dimethylaminoethyl, 2-dimethylaminoethyl and 3-dimethylaminopropyl.

Suitable values for $R^1$ or Q and suitable values for a substituent on $R^1$ or Q include:

for aryl-(1–6C)alkyl: benzyl, 2-phenylethyl, 2-phenylpropyl and 3-phenylpropyl;
for aryl-(1–6C)alkoxy: benzyloxy and 2-phenylethoxy;
for aryloxy: phenoxy and 2-naphthyloxy;
for arylamino: anilino;
for N-(1–6C)alkyl-arylamino: N-methylanilino and N-ethylanilino;
for aryl-(1–6C)alkylamino: benzylamino, 2-phenethylamino, 2-phenylpropylamino and 3-phenylpropylamino;
for N-(1–6C)alkyl-aryl-(1–6C)alkylamino: N-benzyl-N-methylamino;
for aroylamino: benzamido and 2-naphthoylamino;
arylsulphonylamino: benzenesulphonylamido;
for N-arylcarbamoyl: N-phenylcarbamoyl;
for N-arylsulphamoyl: N-phenylsulphamoyl;
for aryl-(2–6C)alkanoylamino: phenylacetamido and 3-phenylpropionamido;
for heteroaryl-(1–6C)alkyl: heteroarylmethyl, 2-heteroarylethyl, 2-heteroarylpropyl and 3-heteroarylpropyl;
for heteroaryl-(1–6C)alkoxy: heteroarylmethoxy and 2-heteroarylethoxy;
for N-(1–6C)alkyl-heteroarylamino: N-methylheteroarylamino;

for heteroaryl-(1–6C)alkylamino: heteroarylmethylamino, 2-heteroarylethylamino and 3-heteroarylpropylamino;

for N-(1–6C)alkyl-heteroaryl-(1–6C)alkylamino: N-methylheteroarylmethylamino and N-methyl-2-heteroarylethylamino;

for heteroaryl-(2–6C)alkanoylamino: heteroarylacetamido and 3-heteroarylpropionamido;

for heteroaryl-(1–6C)alkoxy-(1–6C)alkyl: heteroarylmethoxymethyl, 2-heteroarylethoxymethyl and 3-heteroarylpropoxymethyl;

for heteroaryl-(1–6C)alkylamino-(1–6C)alkyl: heteroarylmethylaminomethyl, 2-heteroarylethylaminomethyl and 3-heteroarylpropylaminomethyl;

for N-(1–6C)alkyl-heteroaryl-(1–6C)alkylamino-(1–6C)alkyl: N-heteroarylmethyl-N-methylaminomethyl, N-(2-heteroarylethyl)-N-methylaminomethyl and N-(3-heteroarylpropyl)-N-methylaminomethyl;

for heterocyclyl-(1–6C)alkyl: heterocyclylmethyl, 2-heterocyclylethyl, 2-heterocyclylpropyl and 3-heterocyclylpropyl;

for heterocyclyl-(1–6C)alkoxy: heterocyclylmethoxy and 2-heterocyclylethoxy;

for N-(1–6C)alkyl-heterocyclylamino: N-methylheterocyclylamino;

for heterocyclyl-(1–6C)alkylamino: heterocyclylmethylamino, 2-heterocyclylethylamino and 3-heterocyclylpropylamino;

for N-(1–6C)alkyl-heterocyclyl-(1–6C)alkylamino: N-methylheterocyclylmethylamino and N-methyl-2-heterocyclylethylamino;

for heterocyclyl-(2–6C)alkanoylamino: heterocyclylacetamido and 3-heterocyclylpropionamido;

for heterocyclyl-(1–6C)alkoxy-(1–6C)alkyl: heterocyclylmethoxymethyl, 2-heterocyclylethoxymethyl and 3-heterocyclylpropoxymethyl;

for heterocyclyl-(1–6C)alkylamino-(1–6C)alkyl: heterocyclylmethylaminomethyl, 2-heterocyclylethylaminomethyl and 3-heterocyclylethylaminomethyl;

for N-(1–6C)alkyl-heterocyclyl-(1–6C)alkylamino-(1–6C)alkyl: N-heterocyclylmethyl-N-methylaminomethyl, N-(2-heterocyclylethyl)-N-methylaminomethyl and N-(3-heterocyclylpropyl)-N-methylaminomethyl;

for (1–3C)alkylenedioxy: methylenedioxy, ethylenedioxy and trimethylenedioxy;

for (1–6C)alkylthio: methylthio, ethylthio and propylthio;

for (1–6C)alkylsulphinyl: methylsulphinyl, ethylsulphinyl and propylsulphinyl;

for (1–6C)alkylsulphonyl: methylsulphonyl, ethylsulphonyl and propylsulphonyl;

for (2–6C)alkanoyloxy: acetoxy and propionyloxy:

for (1–6C)alkanyloylamino: formamido, acetamido and propionamido;

for N-(1–6C)alkylsulphamoyl: N-methylsulphamoyl and N-ethylsulphamoyl;

for N,N-di-[(1–6C)alkyl]sulphamoyl: N,N-dimethylsulphamoyl;

for (1–6C)alkanesulphonylamino: methanesulphoylamino and ethanesulphonylamino;

for N-(1–6C)alkyl-(1–6C)alkanesulphonylamino: N-methylmethanesulphonylamino and N-methylethanesulphonylamino;

for carboxy-(1–6C)alkyl: carboxymethyl, 1-carboxyethyl, 2-carboxyethyl, 3-carboxypropyl and 4-carboxybutyl;

for (1–6C)alkoxycarbonyl-(1–6C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;

for carbamoyl-(1–6C)alkyl: carbamoylmethyl, 1-carbamoylethyl, 2-carbamoylethyl and 3-carbamoylpropyl;

for N-(1–6C)alkylcarbamoyl-(1–6C)alkyl: N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;

for N,N-di-[(1–6C)alkyl]carbamoyl-(1–6C)alkyl: N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl, 3-(N,N-dimethylcarbamoyl)propyl and 4-(N,N-dimethylcarbamoyl)butyl;

for halogeno-(2–6C)alkoxy: 2-chloroethoxy, 2-bromoethoxy, 3-chloropropoxy, 1,1,2,2-tetrafluoroethoxy and 2,2,2-trifluoroethoxy;

for hydroxy-(2–6C)alkoxy: 2-hydroxyethoxy, 3-hydroxypropoxy, 2-hydroxy-1-methylethoxy,2-hydroxy-2-propoxy and 4-hydroxybutoxy;

for (1–6C)alkoxy-(2–6C)alkoxy: 2-methoxyethoxy, 2-ethoxyethoxy, 3-methoxypropoxy, 2-methoxy-1-methylethoxy and 4-ethoxybutoxy;

for cyano-(1–6C)alkoxy: cyanometyloxy, 2-cyanoethoxy and 3-cyanopropoxy;

for carboxy-(1–6C)alkoxy: carboxymethoxy, 1-carboxyethoxy, 2-carboxyethoxy and 3-carboxypropoxy;

for (1–6C)alkoxycarbonyl-(1–6C)alkoxy: methoxycarbonylmethoxy, ethoxycarbonylmethoxy, tert-butoxycarbonylmethoxy, 2-methoxycarbonylethoxy and 3-ethoxycarbonylpropoxy;

for carbamoyl-(1–6C)alkoxy: carbamoylmethoxy and 2-carbamoylethoxy;

for N-(1–6C)alkylcarbamoyl-(1–6C)alkoxy: N-methylcarbamoylmethoxy, 2-(N-ethylcarbamoyl)ethoxy and 3-(N-methylcarbamoyl)propoxy;

for N,N-di-[(1–6C)alkyl]carbamoyl-(1–6C)alkoxy: N,N-dimethylcarbamoylmethyl, 2-(N,N-dimethylcarbamoyl)ethoxy and 3-(N,N-diethylcarbamoyl)propoxy;

for amino-(2–6C)alkoxy: 2-aminoethoxy, 2-amino-1-methylethoxy, 3-aminopropoxy, 2-amino-2-methylpropoxy and 4-aminobutoxy;

for (1–6C)alkylamino-(2–6C)alkoxy: 2-methylaminoethoxy, 2-methylamino-1-methylethoxy and 3-ethylaminopropoxy;

for di-[(1–6C)alkyl]amino-(2–6C)alkoxy: 2-dimethylaminoethoxy, 2-diethylaminoethoxy, 2-dimethylaminopropoxy, 2-dimethylamino-2-methylethoxy, 3-dimethylaminopropoxy and 4-dimethylaminobutoxy;

for halogeno-(2–6C)alkylamino: 2-fluoroethylamino, 2-chloroethylamino, 2-bromoethylamino, 3-fluoropropylamino and 3)-chloropropylamino;

for hydroxy-(2–6C)alkylamino: 2-hydroxyethylamino, 3-hydroxypropylamino, 2-hydroxy-2-methylpropylamino and 4-hydroxybutylamino;

for (1–6C)alkoxy-(2–6C)alkylamino: 2-methoxyethylamine, 2-ethoxyethylamino, 3-methoxypropylamino and 3-ethoxypropylamino;

for cyano-(1–6C)alkylamino: cyanomethylamino, 2-cyanoethylamino and 3-cyanopropylamino;
for carboxy-(1–6C)alkylamino: carboxymethylamino, 1-carboxyethylamino, 2-carboxyethylamino and 3-carboxypropylamino;
for (1–6C)alkoxycarbonyl-(1–6C)alkylamino: methoxycarbonylmethylamino, 2-(ethoxycarbonyl)ethylamino and 3-(tert-butoxycarbonyl)propylamino;
for carbamoyl-(1–6C)alkylamino: carbamoylmethylamino and 2-carbamoylethylamino;
for N-(1–6C)alkylcarbamoyl-(1–6C)alkylamino: N-methylcarbamoylmethylamino, N-ethylcarbamoylmethylamino and 2-(N-methylcarbamoyl)ethylamino;
for N,N-di-[(1–6C)alkyl]carbamoyl-(1–6C)alkylamino: N,N-dimethylcarbamoylmethylamino, N,N-diethylcarbamoylmethylamino and 2-(N,N-dimethylcarbamoyl)ethylamino;
for amino-(2–6C)alkylamino: 2-aminoethylamino, 3-aminopropylamino, 2-amino-2-methylpropylamino and 4-aminobutylamino;
for (1–6C)alkylamino-(2–6C)alkylamino: 2-methylaminoethylamino, 2-ethylaminoethylamino, 2-propylaminoethylamino, 3-methylaminopropylamino, 3-ethylaminopropylamino, 2-methylamino-2-methylpropylamino and 4-methylaminobutylamino;
for di-[(1–6C)alkyl]amino-(2–6C)alkylamino: 2-dimethylaminoethylamino, 2-(N-ethyl-N-methylamino)ethylamino, 2-dimethylaminoethylamino, 2-dipropylaminoethylamino, 3-dimethylaminopropylamino, 3-diethylaminopropylamino, 2-dimethylamino-2-methylpropylamino and 4-dimethylaminobutylamino;
for N-(1–6C)alkyl-halogeno-(2–6C)alkylamino: N-(2-chloroethyl)-N-methylamino, N-(2-bromoethyl)-N-methylamino and N-(2-bromoethyl)-N-ethylamino;
for N-(1–6C)alkyl-hydroxy-(2–6C)-alkylamino: N-(2-hydroxyethyl)-N-methylamino, N-(3-hydroxypropyl)-N-methylamino and N-ethyl-N-(2-hydroxyethyl)amino;
for N-(1–6C)alkyl-(1–6C)alkoxy-(2–6C)alkylamino: N-methyl-N-(2-methoxyethyl)amino, N-methyl-N-(3-methoxypropyl)amino and N-ethyl-N-(2-methoxyethyl)amino;
for N-(1–6C)alkyl-cyano-(1–6C)alkylamino: N-(cyanomethyl)-N-methylamino;
for N-(1–6C)alkyl-carboxy-(1–6C)alkylamino: N-carboxymethyl-N-methylamino and N-(2-carboxyethyl)-N-methylamino;
for N-(1–6C)alkyl-(1–6C)alkoxycarbonyl-(1–6C)alkylamino: N-methoxycarbonylmethyl-N-methylamino, N-(2-ethoxycarbonylethyl)-N-ethylamino and N-(2-tert-butoxycarbonylethyl)-N-methylamino;
for N-(1–6C)alkyl-carbamoyl-(1–6C)alkylamino: N-carbamoylmethyl-N-methylamino and N-(2-carbamoylmethyl)-N-methylamino;
for N-(1–6C)alkyl-N-(1–6C)alkylcarbamoyl-(1–6C)alkylamino: N-(N-methylcarbamoylmethyl)-N-methylamino, N-(N-ethylcarbamoylmethyl)-N-methylamino and N-[2-(N-methylcarbamoyl)ethyl]-N-methylamino;
for N-(1–6C)alkyl-N,N-di-[(1–6C)alkyl]carbamoyl-(1–6C)alkylamino: N-(N,N-dimethylcarbamoylmethyl)-N-methylamino and N-[2-(N,N-dimethylcarbamoyl)ethyl]-N-methylamino;
for N-(1–6C)alkyl-amino-(2–6C)alkylamino: N-(2-aminoethyl)-N-methylamino, N-(3-aminopropyl)-N-methylamino and N-(4-aminobutyl)-N-methylamino;
for N-(1–6C)alkyl-(1–6C)alkylamino-(2–6C)alkylamino: N-(2-methylaminoethyl)-N-methylamino, N-(2-methylaminoethyl)-N-methylamino, N-(3-methylaminopropyl)-N-methylamino, N-(3-ethylaminopropyl)-N-ethylamino and N-(4-methylaminobutyl)-N-methylamino;
for N-(1–6C)alkyl-di-[(1–6C)alkyl]amino-(2–6C)alkylamino: N-(2-dimethylaminoethyl)-N-methylamino, N-(2-diethylaminoethyl)-N-methylamino, N-(3-dimethylaminopropyl)-N-methylamino and N-(4-dimethylaminobutyl)-N-methylamino;
for halogeno-(2–6C)alkanoylamino: 2-chloroacetamido and 3-chloropropionamido;
for hydroxy-(2–6C)alkanoylamino: 2-hydroxyacetamido and 3-hydroxypropionamido;
for (1–6C)alkoxy-(2–6C)alkanoylamino: 2-methoxyacetamido and 3-methoxypropionamido;
for cyano-(2–6C)alkanoylamino: 2-cyanoacetamido and 3-cyanopropionamido;
for carboxy-(2–6C)alkanoylamino: 2-carboxyacetamido and 3-carboxypropionamido;
for (1–6C)alkoxycarbonyl-(2–6C)alkanoylamino: 2-methoxycarbonylacetamido, 2-(tert-butoxycarbonyl)acetamido and 3-methoxycarbonylpropionamido;
for carbamoyl-(2–6C)alkanoylamino: 2-carbamoylacetamido, 3-carbamoylpropionamido and 4-carbamoylbutyramido;
for N-(1–6C)alkylcarbamoyl-(2–6C)alkanoylamino: 2-(N-methylcarbamoyl)acetamido and 3-(N-ethylcarbamoyl)propionamido;
for N,N-di-[(1–6C)alkyl]carbamoyl-(2–6C)alkanoylamino: 2-(N,N-dimethylcarbamoyl)acetamido, 2-(N,N-diethylcarbamoyl)acetamido and 3-(N,N-dimethylcarbamoyl)propionamido;
for amino-(2–6C)alkanoylamino: 2-aminoacetamido, 2-aminopropionamido and 3-aminopropionamino;
for (1–6C)alkylamino-(2–6C)alkanoylamino: 2-methylaminoacetamido, 2-ethylaminoacetamido, 2-methylaminopropionamido and 3-methylaminopropionamido;
for di-[(1–6C)alkyl]amino-(2–6C)alkanoylamino: 2-dimethylaminoacetamido, 2-diethylaminoacetamido, 2-dimethylaminopropionamido and 3-dimethylaminopropionamido.

When, as defined hereinbefore, any of the substituents on $R^1$ or Q which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino, di-[(1–6C)alkyl]amino and heterocyclyl, suitable substituents so formed include, for example, substituted heterocyclyl-(1–6C)alkoxy groups such as 2-hydroxy-3-piperidinopropoxy and 2-hydroxy-3-morpholinopropoxy, substituted amino-(2–6C)alkoxy groups such as 3-amino-2-hydroxypropoxy, substituted (1–6C)alkylamino-(2–6C)alkoxy groups such as 2-hydroxy-3-methylaminopropoxy, substituted di-[(1–6C)alkyl]amino-(2–6C)alkoxy groups such as 3-dimethylamino-2-hydroxypropoxy, 3-[N-(3-dimethylaminopropyl)-N-methylamino]propoxy and 3-[N-(3-dimethylaminopropyl)-N-methylamino]-2-hydroxypropoxy, substituted heterocyclyl-(1–6C)alkylamino groups such as 2-hydroxy-3-piperidinopropylamino and 2-hydroxy-3-morpholinopropylamino, substituted amino-(2–6C)alkylamino groups such as 3-amino-2-hydroxypropylamino, substituted (1–6C)alkylamino-(2–6C)alkylamino groups such as 2-hydroxy-3-methylaminopropylamino, substituted di-[(1–6C)alkyl]amino-(2–6C)alkylamino groups such as 3-dimethylamino-2-hydroxypropylamino, 3-[N-(3-dimethylaminopropyl)-N-methylamino]propylamino and 3-[N-(3-dimethylaminopropyl)-N-methylamino]-2-hydroxypropylamino and substituted (1–6C)alkylamino-(1–6C)alkyl groups such as 2-dimethylaminoethylaminomethyl, 3-dimethylaminopropylaminomethyl, 3-dimethylamino-2,2-dimethylpropylaminomethyl, 2-morpholinoethylaminomethyl, 2-piperazin-1-ylethylaminomethyl and 3-morpholinopropylaminomethyl.

For the avoidance of any doubt it is to be understood that, when X or Y is a CH group and the ring in which the X and Y groups are embedded bears one or more $R^1$ substituents, a $R^1$ substituent may be located at any suitable location on that ring including on the carbon atom at the X or Y position.

A suitable pharmaceutically-acceptable salt of a compound of the Formula I is, for example, an acid-addition salt of a compound of the Formula I which is sufficiently basic, for example an acid-addition salt with an inorganic or organic acid such as hydrochloric, hydrobromic, sulphuric, trifluoroacetic, citric or maleic acid; or, for example a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Various forms of prodrugs are known in the art. For examples of such prodrug. derivatives, see:
a) Design of Prodrugs, edited by H. Bundgaard, (Elsevier, 1985) and *Methods in Enzymology*, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, *Advanced Drug Delivery Reviews*, 8, 1–38 (1992);
d) H. Bundgaard, et al., *Journal of Pharmaceutical Sciences*, 77, 285 (1988); and
e) N. Kakeya, et al., *Chem. Pharm. Bull.*, 32, 692 (1984).

Examples of such pro-drugs may be used to form in-vivo-cleavable esters of a compound of the Formula I. An in-vivo-cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include (1–6C)alkoxymethyl esters, for example methoxymethyl; (1–6C)alkanoyloxymethyl esters, for example pivaloyloxymethyl; phthalidyl esters; (3–8C)cycloalkoxycarbonyloxy(1–6C)alkyl esters, for example 1-cyclohexylcarbonyloxyethyl; 1,3-dioxolan-2-ylmethyl esters, for example 5-methyl-1,3-dioxolan-2-ylmethyl; and (1–6C)alkoxycarbonyloxyethyl esters, for example 1-methoxycarbonyloxyethyl; and may be formed at any carboxy group in the compounds of this invention.

Particular novel compounds of the first aspect of the invention include, for example, amide derivatives of the Formula I, or pharmaceutically-acceptable salts thereof, wherein:

(a) $R^3$ is hydrogen, halogeno (such as fluoro, chloro or bromo) or (1–6C)alkyl (such as methyl, ethyl, propyl and isopropyl), preferably $R^3$ is hydrogen, chloro, methyl or ethyl, more preferably hydrogen, chloro or methyl; and X, Y, $R^1$, $R^2$, Q, m, n and q have any of the meanings defined hereinbefore or in this section relating to particular novel compounds of the invention;

(b) Q is phenyl or a heteroaromatic 5- or 6-membered monocyclic ring or a 9- or 10-membered bicyclic ring with up to five ring heteroatoms selected from oxygen, nitrogen and sulphur which bears a basic substituent selected from the substituents for Q defined hereinbefore; and X, Y, $R^1$, $R^2$, $R^3$, m, n and q have any of the meanings defined hereinbefore or in this section relating to particular novel compounds of the invention;

(c) Q is phenyl, indenyl, indanyl or fluorenyl which optionally bears 1, 2 or 3 substituents selected from the substituents for Q defined hereinbefore, and X, Y, $R^1$, $R^2$, $R^3$, m, n and q have any of the meanings defined hereinbefore or in this section relating to particular novel compounds of the invention;

(d) Q is phenyl or a heteroaromatic 5- or 6-membered monocyclic ring or a 9- or 10-membered bicyclic ring with up to five ring heteroatoms selected from oxygen, nitrogen and sulphur which bears a basic substituent selected from amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C)alkylamino, (1–6C)alkylamino-(2–6C)alkylamino, di-[(1–6C)alkyl]amino-(2–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, amino-(2–6C)alkanoylamino, (1–6C)alkylamino-(2–6C)alkanoylamino, di-[(1–6C)alkyl]amino-(2–6C)alkanoylamino, heteroaryl, heteroaryl-(1–6C)alkyl, heteroaryl-(1–6C)alkoxy, heterocyclyl, heterocyclyl-(1–6C)alkyl and heterocyclyl-(1–6C)alkoxy, and wherein any heteroaryl or heterocyclyl group in a basic substituent on Q may optionally bear 1 or 2 substituents selected from halogeno, (1–6C)alkyl, (2–6C)alkanoyl, amino, (1–6C)alkylamino and di-[(1–6C)alkyl]amino; and X, Y, $R^1$, $R^2$, $R^3$, m, n and q have any of the meanings defined hereinbefore or in this section relating to particular novel compounds of the invention;

(e) Q is phenyl or a heteroaromatic 5- or 6-membered monocyclic ring or a 9- or 10-membered bicyclic ring with up to five ring heteroatoms selected from oxygen, nitrogen and sulphur which optionally bears 1, 2 or 3 substituents selected from hydroxy, halogeno, trifluoromethyl, cyano, nitro, amino, carboxy, (1–6C)alkyl, (1–6C)alkoxy, (1–6C)alkylamino, di-[(1–6C)alkyl]amino, (1–6C)alkoxycarbonyl, (2–6C)alkanoyl, halogeno-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, amino-(2–6C)alkoxy, (1–6C)alkylamino-(2–6C)alkoxy, di-[(1–6C)alkyl]amino-(2–6C)alkoxy, pyridyl, imidazolyl, pyridyl-(1–6C)alkyl, imidazolyl-(1–6C)alkyl, pyridyl-(1–6C)alkoxy, imidazolyl-(1–6C)alkoxy, pyrrolidinyl, piperidinyl, morpholinyl, piperazinyl, 4-(1–6C)alkylpiperazinyl, 4-(2–6C)alkanoylpiperazinyl, pyrrolidinyl-(1–6C)alkyl, piperidinyl-(1–6C)alkyl, morpholinyl-(1–6C)alkyl, piperazinyl-(1–6C)alkyl, 4-(1–6C)alkylpiperazinyl-(1–6C)alkyl, 4-(2–6C)

alkanoylpiperazinyl-(1–6C)alkyl, pyrrolidinyloxy, piperidinyloxy, 1-(1–6C)alkylpiperidinyloxy, pyrrolidinyl-(2–6C)alkoxy, piperidinyl-(2–6C)alkoxy, morpholinyl-(2–6C)alkoxy, piperazinyl-(2–6C)alkoxy, 4-(1–6C)alkylpiperazinyl-(2–6C)alkoxy and 4-(2–6C) alkanoylpiperazinyl-(2–6C)alkoxy or Q bears a (1–3C) alkylenedioxy substituent; and X, Y, $R^1$, $R^2$, $R^3$, m, n and q have any of the meanings defined hereinbefore or in this section relating to particular novel compounds of the invention;

(f) Q is phenyl, indenyl, indanyl, fluorenyl or a heteroaromatic 5- or 6-membered monocyclic ring with up to three ring heteroatoms selected from oxygen, nitrogen and sulphur which optionally bears 1, 2 or 3 substituents selected from hydroxy, halogeno, trifluoromethyl, cyano, nitro, amino, carboxy, (1–6C)alkyl, (1–6C)alkoxy, (1–6C)alkylamino, di-[(1–6C)alkyl]amino, (1–6C)alkoxycarbonyl, (2–6C)alkanoyl, (1–6C)alkanoylamino, (1–6C)alkanesulphonylamino, $\underline{N}$-(1–6C)alkyl-(1–6C)alkanesulphonylamino, phenyl, furyl, thienyl, azetidinyl, pyrrolinyl, pyrrolidinyl, 1,1-dioxidoisothiazolidinyl, piperidinyl, homopiperidinyl, morpholinyl, piperazinyl, homopiperazinyl, pyrrolidinyl-(1–6C)alkyl, piperidinyl-(1–6C)alkyl, morpholinyl-(1–6C)alkyl and piperazinyl-(1–6C)alkyl, and wherein any phenyl, furyl, thienyl or heterocyclyl group in a substituent on Q may optionally bear 1 or 2 substituents selected from halogeno, (1–6C)alkyl, (1–6C)alkoxy and (2–6C)alkanoyl; and X, Y, $R^1$, $R^2$, $R^3$, m, n and q have any of the meanings defined hereinbefore or in this section relating to particular novel compounds of the invention;

(g) Q is phenyl, furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinoyl, quinazolinyl, quinoxalinyl or naphthyridinyl which optionally bears 1 or 2 substituents selected from those defined in paragraph (b), (d) or (e) hereinbefore; and X, Y, $R^1$, $R^2$, $R^3$, m, n and q have any of the meanings defined hereinbefore or in this section relating to particular novel compounds of the invention;

(h) Q is phenyl, 2- or 3-furyl, 2- or 3-thienyl, 2-, 4- or 5-oxazolyl, 3-, 4- or 5-isoxazolyl, 2-, 4- or 5-imidazolyl, 3- or 4-pyrazolyl, 2-, 4- or 5-thiazolyl, 3-, 4- or 5-isoxazolyl, 2-, 3- or 4-pyridyl, 3- or 4-pyridazinyl, 2-, 4- or 5-pyrimidinyl, 2-pyrazinyl, 2-, 3-, 5- or 6-benzofuranyl, 2-, 3-, 5- or 6-indolyl, 2-, 3-, 5- or 6-benzothienyl, 2-, 5- or 6-benzoxazolyl, 2-, 5- or 6-benzimidazolyl, 2-, 5- or 6-benzothiazolyl, 3-, 5- or 6-indazolyl, 5-benzofurazanyl, 2-, 3-, 6- or 7-quinolyl, 3-, 6- or 7-isoquinolyl, 2-, 6- or 7-quinazolinyl, 2-, 6- or 7-quinoxalinyl, or 1,8-naphthyridin-2-yl or 1,8-naphthyridin-3-yl which optionally bears 1 or 2 substituents selected from those defined in paragraph (b), (d) or (e) hereinbefore; and X, Y, $R^1$, $R^2$, $R^3$, m, n and q have any of the meanings defined hereinbefore or in this section relating to particular novel compounds of the invention;

(i) Q is a heteroaromatic 5- or 6-membered monocyclic ring, a 9- or 10-membered bicyclic ring or a 13- or 14-membered tricyclic ring each with up to five ring heteroatoms selected from oxygen, nitrogen and sulphur which optionally bears 1, 2 or 3 substituents selected from hydroxy, halogeno, trifluoromethyl, cyano, nitro, amino, carboxy, (1–6C)alkyl, (1–6C)alkoxy, (1–3C)alkylenedioxy, (1–6C)alkylamino, di-[(1–6C)alkyl]amino and (1–6C)alkoxycarbonyl; and X, Y, $R^1$, $R^2$, $R^3$, m, n and q have any of the meanings defined hereinbefore or in this section relating to particular novel compounds of the invention;

(j) Q is a heteroaromatic 13- or 14-membered tricyclic ring each with up to five ring heteroatoms selected from oxygen, nitrogen and sulphur which optionally bears 1, 2 or 3 substituents selected from hydroxy, halogeno, trifluoromethyl, cyano, nitro, amino, carboxy, (1–6C)alkyl, (1–6C)alkoxy, (1–3C)alkylenedioxy, (1–6C)alkylamino, di-[(1–6C)alkyl]amino and (1–6C)alkoxycarbonyl; and X, Y, $R^1$, $R^2$, $R^3$, m, n and q have any of the meanings defined hereinbefore or in this section relating to particular novel compounds of the invention;

(k) Q is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothiophenyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl which optionally bears 1 or 2 substituents selected from those defined in paragraph (i) hereinbefore; and X, Y, $R^1$, $R^2$, $R^3$, m, n and q have any of the meanings defined hereinbefore or in this section relating to particular novel compounds of the invention;

(l) Q is 1-, 2- or 3-carbazolyl, 1-, 2-, 3- or 4-dibenzofuranyl or 1-, 2-, 3- or 4-dibenzothiophenyl which optionally bears 1 or 2 substituents selected from those defined in paragraph (i) hereinbefore; and X Y, $R^1$, $R^2$, $R^3$, m, n and q have any of the meanings defined hereinbefore or in this section relating to particular novel compounds of the invention;

(m) n is 0; and X, Y, $R^1$, $R^3$, Q, m and q have any of the meanings defined hereinbefore or in this section relating to particular novel compounds of the invention;

(n) n is 1 and $R^2$ is halogeno or (1–6C)alkyl; and X, Y, $R^1$, $R^3$, Q, m and q have any of the meanings defined hereinbefore or in this section relating to particular novel compounds of the invention;

(o) q is 0, and X, Y, $R^1$, $R^2$, $R^3$, Q, m and n have any of the meanings defined hereinbefore or in this section relating to particular novel compounds of the invention;

(p) m is 1 and $R^1$ is amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C)alkylamino, (1–6C)alkylamino-(2–6C)alkylamino, di-[(1–6C)alkyl]amino-(2–6C)alkylamino, $\underline{N}$-(1–6C)alkyl-amino-(2–6C)alkylamino, $\underline{N}$-(1–6C)alkyl-(1–6C)alkylamino-(2–6C)alkylamino, $\underline{N}$-(1–6C)alkyl-di-[(1–6C)alkyl]amino-(2–6C)alkylamino, heteroaryl, heteroaryl-(1–6C)alkyl, heteroaryl-(1–6C)alkoxy, heterocyclyl, heterocyclyl-(1–6C)alkyl, heterocyclyloxy or heterocyclyl-(1–6C)alkoxy, and wherein any heteroaryl or heterocyclyl group in a $R^1$ substituent may optionally bear 1 or 2 substituents selected from hydroxy, halogeno, (1–6C)alkyl, (1–6C)alkoxy, (2–6C)alkanoyl, amino, (1–6C)alkylamino and di-[(1–6C)alkyl]amino; and X, Y, $R^2$, $R^3$, Q, n and q have any of the meanings defined hereinbefore or in this section relating to particular novel compounds of the invention;

(q) m is 1 and $R^1$ is amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C)alkylamino, (1–6C)alkylamino-(2–6C)alkylamino, di-[(1–6C)alkyl]amino-(2–6C)alkylamino, $\underline{N}$-(1–6C)alkyl-amino-(2–6C)alkylamino, $\underline{N}$-(1–6C)alkyl-(1–6C)alkylamino-(2–6C)

alkylamino, N-(1–6C)alkyl-di-[(1–6C)alkyl]amino-(2–6C) alkylamino, pyridyl, imidazolyl, pyridyl-(1–6C)alkyl, imidazolyl-(1–6C)alkyl, pyridyl-(1–6C)alkoxy, imidazolyl-(1–6C)alkoxy, pyrrolidinyl, piperidinyl, morpholinyl, piperazinyl, 4-(1–6C)alkylpiperazinyl, homopiperazinyl, 4-(1–6C)alkylhomopiperazinyl, 4-(2–6C)alkanoylpiperazinyl, pyrrolidinyl-(1–6C)alkyl, piperidinyl-(1–6C)alkyl, morpholinyl-(1–6C)alkyl, piperazinyl-(1–6C)alkyl, 4-(1–6C)alkylpiperazinyl-(1–6C)alkyl, 4-(2–6C)alkanoylpiperazinyl-(1–6C)alkyl, pyrrolidinyloxy, piperidinyloxy, 1-(1–6C)alkylpiperidinyloxy, pyrrolidinyl-(2–6C)alkoxy, piperidinyl-(2–6C)alkoxy, morpholinyl-(2–6C)alkoxy, piperazinyl-(2–6C)alkoxy, 4-(1–6C)alkylpiperazinyl-(2–6C)alkoxy or 4-(2–6C)alkanoylpiperazinyl-(2–6C)alkoxy; and X, Y, $R^2$, $R^3$, Q, n and q have any of the meanings defined hereinbefore or in this section relating to particular novel compounds of the invention;

(r) m is 1 and $R^1$ is hydroxy, halogeno, trifluoromethyl, cyano, mercapto, nitro, carboxy, (1–6C)alkoxycarbonyl, (1–6C)alkyl or (1–6C)alkoxy; and X, Y, $R^2$, $R^3$, Q, n and q have any of the meanings defined hereinbefore or in this section relating to particular novel compounds of the invention;

(s) m is 2 and the first $R^1$ substituent is selected from the substituents specified in paragraph (q) hereinbefore and the second $R^1$ substituent is selected from the substituents specified in paragraph (r) hereinbefore: and X, Y, $R^2$, $R^3$, Q, n and q have any of the meanings defined hereinbefore or in this section relating to particular novel compounds of the invention;

(t) each of X and Y is a CH group; and $R^1$, $R^2$, $R^3$, Q, m, n and q have any of the meanings defined hereinbefore or in this section relating to particular novel compounds of the invention; and (u) one or both of X and Y is a N group; and $R^1$, $R^2$, $R^3$, Q, m, n and q have any of the meanings defined hereinbefore or in this section relating to particular-novel compounds of the invention.

Particular novel compounds of the second aspect of the invention include, for example, amide derivatives of the Formula I, or pharmaceutically-acceptable salts thereof, wherein:

(a) $R^3$ is halogeno (such as fluoro, chloro or bromo) or (1–6C)alkyl (such as methyl, ethyl, propyl and isopropyl), preferably $R^3$ is chloro, methyl or ethyl, more preferably chloro or methyl; and X, Y, $R^1$, $R^2$, Q, m, n and q have any of the meanings defined hereinbefore.

A preferred compound of the first aspect of the invention is an amide derivative of the Formula I wherein X is CH or N;

Y is CH or N;

$R^3$ is hydrogen, fluoro, chloro, bromo, methyl or ethyl;

m is 0, 1 or 2;

$R^1$ is hydroxy, fluoro, chloro, bromo, trifluoromethyl, cyano, methyl, ethyl, propyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methyl aminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-(2-dimethylaminoethyl)-N-methylamino, N-(2-diethylaminoethyl)-N-methylamino, N-(3-dimethylaminopropyl)-N-methylamino, N-(3-diethylaminopropyl)-N-methylamino, pyridyl, pyridylmethyl, pyridylmethoxy, pyrrolidinyl, piperidinyl, morpholinyl, piperazinyl, 4-methylpiperazinyl, homopiperazinyl, 4-methylhomopiperazinyl, 4-acetylpiperazinyl, pyrrolidinylmethyl, piperidinylmethyl, morpholinylmethyl, piperazinylmethyl, 4-methylpiperazinylmethyl, 4-acetylpiperazinylmethyl, pyrrolidinyloxy, 1-methylpyrrolidinyloxy, piperidinyloxy, 1-methylpiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy or 3-(4-acetylpiperazinyl)propoxy;

n is 0 or 1;

$R^2$ is fluoro, chloro, bromo, methyl or ethyl;

q is 0; and

Q is phenyl, furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, pyridyl, pyridylmethyl, pyridylmethoxy, pyrrolidinyl, piperidinyl, morpholinyl, piperazinyl, 4-methylpiperazinyl, homopiperazinyl, 4-methylhomopiperazinyl, 4-acetylpiperazinyl, pyrrolidinylmethyl, piperidinylmethyl, morpholinylmethyl, piperazinylmethyl, 4-methylpiperazinylmethyl, 4-acetylpiperazinylmethyl, pyrrolidinyloxy, 1-methylpyrrolidinyloxy, piperidinyloxy, 1-methylpiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy and 3-(4-acetylpiperazinyl)propoxy;

or a pharmaceutically-acceptable salt thereof.

A further preferred compound of the first aspect of the invention is an amide derivative of the Formula I wherein X is CH;

Y is CH or N;

$R^3$ is hydrogen, chloro or methyl;

m is 0, 1 or 2;

$R^1$ is hydroxy, fluoro, chloro, bromo, trifluoromethyl, cyano, methyl, ethyl, propyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino 3-ethylaminopropylamino, 2-dimethylaminoethylamino, 2-diethylaminoethylamino 3-dimethylaminopropylamino, 3-diethylaminopropylamino, N-(2-aminoethyl)-N-methylamino, N-(3-aminopropyl)-N-methylamino, N-(2-methylaminoethyl)-N-(N-methylamino, N-(2-ethylaminoethyl)-N-methylamino, N-(3-methylaminopropoxy)-N-methylamino, N-(3-ethylaminopropyl)-N-methylamino, N-(2-dimethylaminoethyl)-N-methylamino, N-(2-diethylaminoethyl )-N-methylamino, N-(3-dimethylaminopropyl)-N-methylamino, N-(3-diethylaminopropyl)-N-methylamino, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy or 3-(4-acetylpiperazin-1-yl)propoxy;

n is 0;

q is 0; and

Q is phenyl, 2-furyl, 2-thienyl, 4-oxazolyl, 5-isoxazolyl, 4-thiazolyl, 5-isothiazolyl, 2-pyridyl 3-pyridyl, 4-pyridyl, 2-benzofuranyl, 2-indolyl, 2-benzothienyl, 2-benzoxazolyl, 2-benzimidazolyl, 2-benzothiazolyl, 4-benzofurazanyl, 2-quinolyl, 6-quinolyl, 7-quinolyl, 3-isoquinolyl, 6-quinazolinyl, 7-quinazolinyl, 6-quinoxalinyl or 7-quinoxalinyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminoethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridyl, 3-pyridyl, 4-pyridyl, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy;

or a pharmaceutically-acceptable salt thereof.

A further preferred compound of the first aspect of the invention is an amide derivative of the Formula I wherein X is CH;

Y is CH or N;

$R^3$ is hydrogen, chloro or methyl;

m is 0, 1 or 2;

$R^1$ is hydroxy, fluoro, chloro, bromo, trifluoromethyl, cyano, methyl, ethyl, propyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-(2-dimethylaminoethyl)-N-methylamino, N-(2-diethylaminoethyl)-N-methylamino, N-(3-dimethylaminopropyl)-N-methylamino, N-(3-diethylaminopropyl)-N-methylamino, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy or 3-(4-acetylpiperazin-1-yl)propoxy;

n is 0;

q is 0; and

Q is phenyl, 2-pyridyl, 3-pyridyl or 4-pyridyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridyl, 3-pyridyl, 4-pyridyl, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy;

or a pharmaceutically-acceptable salt thereof.

A further preferred compound of the first aspect of the invention is an amide derivative of the Formula I wherein X is CH;

Y is CH or N, $R^3$ is hydrogen, chloro or methyl;

m is 1 or 2;

$R^1$ is hydroxy, fluoro, chloro, methyl, ethyl, propyl, methoxy, dimethylaminomethyl, diethylaminomethyl, 2-dimethylaminoethoxy, 2-diethylaminoethoxy, 3-dimethylaminopropoxy, 3-diethylaminopropoxy, 3-dimethylamino-2-hydroxypropoxy, 3-diethylamino-2-hydroxypropoxy, 2-aminoethylamino, 3-aminopropylamino, 4-aminobutylamino, 3-methylaminopropylamino, 2-dimethylaminoethylamino, 2-diethylaminoethylamino, 3-dimethylaminopropylamino, 4-dimethylaminobutylamino, 3-amino-2-hydroxypropylamino, 3-dimethylamino-2-hydroxypropylamino, N-(2-dimethylaminoethyl)-N-methylamino, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, 4-(2-hydroxyethyl)piperazin-1-yl, homopiperazin-1-yl, 4-methylhomopiperazin-1-yl, piperazin-1-ylmethyl, 4-methylpiperazin-1-ylmethyl, homopiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, 4-(2-hydroxyethyl)piperazin-1-ylmethyl, pyrrolidin-3-yloxy, 1-methylpyrrolidin-3-yloxy, piperidin-4-yloxy, 1-methylpiperidin-4-yloxy, 1-benzylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-hydroxy-3-pyrrolidin-1-ylpropoxy, 2-hydroxy-3-piperidinopropoxy, 2-hydroxy-3-morpholinopropoxy, piperidin-4-ylamino, 1-methylpiperidin-4-ylamino, 1-benzylpiperidin-4-ylamino, 2-pyrrolidin-1-ylethylamino, 3-pyrrolidin-1ylpropylamino, 2-morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino, 3-(4-methylpiperazin-1-yl)propylamino, 2-(1-methylpyrrolidin-2-yl)ethylamino, 3-(1-methylpyrrolidin-2-yl)propylamino, 2-dimethylaminoethylaminomethyl, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl) aminomethyl or 2-pyridylmethoxy;

n is 0;

q is 0; and

Q is 2-pyridyl, 3-pyridyl or 4-pyridyl which bears a substituent selected from pyrrolidin-1-yl, 3-hydroxypyrrolidin-1-yl, 2-hydroxymethylpyrrolidin-1-yl, morpholino, piperidino, 4-hydroxypiperidin-1-yl, piperazin-1-yl and 4-methylpiperazin-1-yl;

or a pharmaceutically-acceptable salt thereof.

An especially preferred compound of the first aspect of the invention is an amide derivative of the Formula I wherein X is CH;

Y is CH or N;

$R^3$ is hydrogen, chloro or methyl;

m is 1 and $R^1$ is selected from diethylaminomethyl, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, homopiperazin-1-yl, 4-methylhomopiperazin-1-yl, piperazin-1-ylmethyl, 4-methylpiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, pyrrolidin-3-yloxy, piperidin-4-yloxy, 2-pyrrolidin-1-ylethoxy, 2-piperidinoethoxy, 2-morpholinoethoxy, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl) aminomethyl and 2-pyridylmethoxy;

n is 0;

q is 0; and

Q is 3-pyridyl or 4-pyridyl which bears a substituent selected from pyrrolidin-1-yl morpholino, piperidino, piperazin-1-yl and 4-methylpiperazin-1yl;

or a pharmaceutically-acceptable salt thereof.

A further especially preferred compound of the first aspect of the invention is an amide derivative of the Formula I wherein X is CH;

Y is CH or N;

$R^3$ is hydrogen, chloro or methyl;

m is 1 and $R^1$ is N-(3-dimethylamitiopropyl)-N-methylamino, 4-methylpiperazin-1-yl, 4-methylhomopiperazin-1-yl, 4-methylpiperazin-1-ylmethyl or pyrrolidin-3-yloxy;

n is 0;

q is 0; and

Q is 2-morpholinopyrid-4yl;

or a pharmaceutically-acceptable salt thereof.

A particular preferred compound of the invention is, for example: N-[3-(4-methylpiperazin-1-ylmethyl)phenyl]-2-methyl-5-(2-morpholinopyrid-4-ylcarbonylamino) benzamide, N-[6-(4-ethylpiperazin-1-yl)pyrid-3-yl]-2-chloro-5-(2-morpholinopyrid-4-ylcarbonylamino) benzamide, N-[6-(4-methylpiperazin-1-yl)pyrid-3-yl]-2)-chloro-5-(2-morpholinopyrid-4-ylcarbonylamino)

benzamide or N-{6-[N-(3-dimethylaminopropyl)-N-methylamino]pyrid-3-yl}-2-chloro-5-(2-morpholinopyrid-4-ylcarbonylamino)benzamide;
or a pharmaceutically-acceptable salt thereof.

A preferred compound of the second aspect of the invention is an amide derivative of the Formula I wherein X is CH or N;
Y is CH or N;
R³ is fluoro, chloro, bromo, methyl or ethyl;
m is 0, 1 or 2;
R¹ is hydroxy, fluoro, chloro, bromo, trifluoromethyl, cyano, methyl, ethyl, methoxy, ethoxy, amino, methylamino, ethylamino, dimethylamino, diethylamino, methylaminomethyl, ethylaminomethyl, dimethylaminoethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-(2-dimethylaminoethyl)-N-methylamino, N-(2-diethylaminoethyl)-N-methylamino, N-(3-dimethylaminopropyl)-N-methylamino, N-(3-diethylaminopropyl)-N-methylamino, pyridyl, pyridylmethyl, pyridylmethoxy, 3-pyrrolinyl, pyrrolidinyl, piperidinyl, homopiperidinyl, morpholinyl, piperazinyl, 4-methylpiperazinyl, 4-ethylpiperazinyl, homopiperazinyl, 4-methylhomopiperazinyl, 4-acetylpiperazinyl, pyrrolidinylmethyl, piperidinylmethyl, morpholinylmethyl, piperazinylmethyl, 4-methylpiperazinylmethyl, homopiperazinylmethyl, 4-methylhomopiperazinylmethyl, 4-acetylpiperazinylmethyl, pyrrolidinyloxy, 1-methylpyrrolidinyloxy, piperidinyloxy, 1-methylpiperidinyloxy, homopiperidinyloxy, 1-methylhomopiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy, 3-(4-acetylpiperazinyl)propoxy, 3-dimethylaminopropylaminomethyl, 3-dimethylamino-2,2-dimethylpropylaminomethyl, 2-(1-methylpyrrolidinylethyl)aminomethyl, 3-pyrrolidinylpropylaminomethyl, 2-morpholinylethylaminomethyl, 3-morpholinylpropylaminomethyl, 2-piperazinylethylaminomethyl, 3-(4-methylpiperazinylpropyl)aminomethyl, pyridylmethoxy, imidazolylmethoxy, thiazolylmethoxy and 2-methylthiazolylmethoxy;
n is 0 or 1;
R² is fluoro, chloro, bromo, methyl or ethyl;
q is 0; and
Q is phenyl, indenyl, indanyl, tetrahydronaphthyl, fluorenyl, furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl which optionally bears 1 or 2 substituents selected from hydroxy, fluoro, chloro, trifluoromethyl, cyano, amino, methyl, ethyl, methoxy, ethoxy, propoxy, isopropoxy, cyclopentyloxy, methylenedioxy, methylamino, ethylamino, dimethylamino, diethylamino, acetamido, propionamido, methanesulphonamido, N-methylmethanesulphonamido, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, phenyl, furyl, thienyl, pyridyl, pyridylmethyl, pyridylmethoxy, azetidinyl, 3-pyrrolinyl, pyrrolidinyl, piperidinyl, homopiperidinyl, morpholinyl, piperazinyl, 4-methylpiperazinyl, homopiperazinyl, 4-methylhomopiperazinyl, 4-acetylpiperazinyl, pyrrolidinylmethyl, piperidinylmethyl, morpholinylmethyl, piperazinylmethyl, 4-methylpiperazinylmethyl, 4-acetylpiperazinylmethyl, pyrrolidinyloxy, 1-methylpyrrolidinyloxy, piperidinyloxy, 1-methylpiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy and 3-(4-acetylpiperazinyl)propoxy, and wherein any phenyl, furyl, thienyl, pyridyl or heterocyclyl group in a substituent on Q may optionally bear 1 or 2 substituents selected from fluoro, chloro, methyl and methoxy;
or a pharmaceutically-acceptable salt thereof.

A further preferred compound of the second aspect of the invention is an amide derivative of the Formula I wherein
X is CH;
Y is CH or N;
R³ is chloro or methyl:
m is 0, 1 or 2;
R¹ is hydroxy, fluoro, chloro, bromo, trifluoromethyl, cyano, methyl, ethyl, propyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-(2-dimethylaminoethyl)-N-methylamino, N-(2-diethylaminoethyl)-N-methylamino, N-(3- dimethylaminopropyl)-N-methylamino, N-(3-diethylaminopropyl)-N-methylamino, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrroldin-3-yloxy, piperidin-4-yloxy, 1-methylpiperidin-4-yloxy, 2-(pyrroldin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy or 3-(4-acetylpiperazin-1-yl)propoxy;

n is 0, q is 0; and

Q is phenyl, 2-furyl, 2-thienyl, 4-oxazolyl, 5-isoxazolyl, 4-thiazolyl, 5-isothiazolyl, 2-pyridyl, 3-pyridyl, 4-pyridyl, 2-benzofuranyl, 2-indolyl, 2-benzothienyl, 2-benzoxazolyl, 2-benzimidazolyl, 2-benzothiazolyl, 4-benzofurazanyl, 2-quinolyl, 6-quinolyl, 7-quinolyl, 3-isoquinolyl, 6-quinazolinyl, 7-quinazolinyl, 6-quinoxalinyl or 7-quinoxalinyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridyl, 3-pyridyl, 4-pyridyl, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy;

or a pharmaceutically-acceptable salt thereof.

A further preferred compound of the second aspect of the invention is an amide derivative of the Formula I wherein X is CH;

Y is CH or N;

$R^3$ is chloro or methyl;

m is 0, 1 or 2;

$R^1$ is hydroxy, fluoro, chloro, bromo, trifluoromethyl, cyano, methyl, ethyl, propyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-(2-dimethylaminoethyl)-N-methylamino, N-(2-diethylaminoethyl)-N-methylamino, N-(3-dimethylaminopropyl)-N-methylamino, N-(3-diethylaminopropyl)-N-methylamino, 2-pyridylmethyl, 3-pyridylmethyl, 4-pyridylmethyl, 2-pyridylmethoxy, 3-pyridylethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy or 3-(4-acetylpiperazin-1-yl)propoxy;

n is 0;

q is 0; and

Q is phenyl, 2-pyridyl, 3-pyridyl or 4-pyridyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridyl, 3-pyridyl, 4-pyridyl, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy;

or a pharmaceutically-acceptable salt thereof.

A further preferred compound of the second aspect of the invention is an amide derivative of the Formula I wherein X is CH;
Y is CH or N;
$R^3$ is chloro or methyl;
m is 1 or 2;
$R^1$ is hydroxy, fluoro, chloro, methyl, ethyl, propyl, methoxy, dimethylaminomethyl, diethylaminomethyl, 2-dimethylaminoethoxy, 2-diethylaminoethoxy, 3-dimethylaminopropoxy, 3-diethylaminopropoxy, 3-dimethylamino-2-hydroxypropoxy, 3-diethylamino-2-hydroxypropoxy, 2-aminoethylamino, 3-aminopropylamino, 4-aminobutylamino, 3-methylaminopropylamino, 2-dimethylaminoethylamino, 2-diethylaminoethylamino, 3-dimethylaminopropylamino, 4-dimethylaminobutylamino, 3-amino-2-hydroxypropylamino, 3-dimethylamino-2-hydroxypropylamino, N-(2-dimethylaminoethyl)-N-methylamino, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, 4-(2-hydroxyethyl)piperazin-1-yl, homopiperazin-1-yl, 4-methylhomopiperazin-1-yl, piperazin-1-ylmethyl, 4-methylpiperazin-1-ylmethyl, homopiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, 4-(2-hydroxyethyl)piperazin-1-ylmethyl, pyrrolidin-3-yloxy, 1-methylpyrrolidin-3-yloxy, piperidin-4-yloxy, 1-methylpiperidin-4-yloxy, 1-benzylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-hydroxy-3-pyrrolidin-1-ylpropoxy, 2-hydroxy-3-piperidinopropoxy, 2-hydroxy-3-morpholinopropoxy, piperidin-4-ylamino, 1-methylpiperidin-4-ylamino, 1-benzylpiperidin-4-ylamino, 2-pyrrolidin-1-ylethylamino, 3-pyrrolidin-1-ylpropylamino, 2-morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino, 3-(4-methylpiperazin-1-yl)propylamino, 2-(1-methylpyrrolidin-2-yl)ethylamino, 3-(1-methylpyrrolidin-2-yl)propylamino, 2-dimethylaminoethylaminomethyl, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl or 2-pyridylmethoxy;
n is 0;
q is 0; and
Q is 2-pyridyl, 3-pyridyl or 4-pyridyl which bears a substituent selected from pyrrolidin-1-yl, 3-hydroxypyrrolidin-1-yl, 2-hydroxymethylpyrrolidin-1-yl, morpholino, piperidino, 4-hydroxypiperidin-1-yl, piperazin-1-yl and 4-methylpiperazin-1yl;
or a pharmaceutically-acceptable salt thereof.

An especially preferred compound of the second aspect of the invention is an amide derivative of the Formula I wherein X is CH;
Y is CH or N;
$R_3$ is chloro or methyl;
m is 1 and $R^1$ is selected from diethylaminomethyl, N-(2-dimethylaminoethyl)-N-methylamino, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, homopiperazin-1-yl, 4-methylhomopiperazin-1-yl, piperazin-1-ylmethyl, 4-methylpiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, pyrrolidin-3-yloxy, piperidin-4-yloxy, 2-pyrrolidin-1-ylethoxy, 2-piperidinoethoxy, 2-morpholinoethoxy, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl and 2-pyridylmethoxy;
n is 0;
q is 0; and
Q is 3-pyridyl or 4-pyridyl which bears a substituent selected from pyrrolidin-1-yl, morpholino, piperidino, piperazin-1-yl and 4-methylpiperazin-1yl;
or a pharmaceutically-acceptable salt thereof.

A further especially preferred compound of the second aspect of the invention is an amide derivative of the Formula I wherein X is CH;
Y is CH or N;
$R^3$ is chloro or methyl;
m is 1 and $R^1$ is selected from diethylaminomethyl, N-(2-dimethylaminoethyl)-N-methylamino, N-(3-dimethylaminopropyl)-N-methylamino, 3-pyrrolin-1-yl, pyrrolidin-1-yl, morpholino, piperidino, homopiperidin-1-yl, piperazin-1-yl, 4-methylpiperazin-1-yl, 4-ethylpiperazin-1-yl, homopiperazin-1-yl, 4-methylhomopiperazin-1-yl, piperazin-1-ylmethyl, 4-methylpiperazin-1-ylmethyl, homopiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, pyrrolidin-3-yloxy, N-methylpyrrolidin-3-yloxy, piperidin-4-yloxy, N-methylpiperidin-4-yloxy, homopiperidin-4-yloxy, N-methylhomopiperidin-4-yloxy, 2-pyrrolidin-1-ylethoxy, 2-piperidinoethoxy, 2-morpholinoethoxy, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl, 2-pyridylmethoxy, 4-thiazolylmethoxy and 2-methylthiazol-4-ylmethoxy;
n is 0;
q is 0; and
Q is phenyl which bears 1 or 2 substituents selected from fluoro, chloro, trifluoromethyl, methoxy, cyclopentyloxy, acetamido, N-methylmethanesulphonamido, 2-furyl, azetidin-1-yl, 3-pyrrolin-1-yl, pyrrolidin-1-yl, morpholino, piperidino, homopiperidino, piperazin-1-yl, homopiperazin-1-yl, 4-methylpiperazin-1-yl and 4-methylhomopiperazin-1-yl,
or Q is 1-fluorenyl or 4-dibenzofuranyl, or Q is 3-pyridyl or 4-pyridyl which bears a substituent selected from azetidin-1-yl, 3-pyrrolin-1-yl pyrrolidin-1-yl, morpholino, piperidino, homopiperidino, piperazin-1-yl, homopiperazin-1-yl, 4-methylpiperazin-1-yl and 4-methylhomopiperazin-1yl;
or a pharmaceutically-acceptable salt thereof.

A further especially preferred compound of the second aspect of the invention is an amide derivative of the Formula I wherein X is CH;

Y is CH or N;

R³ is chloro or methyl;

m is 1 and R¹ is $\underline{N}$-(2-dimethylaminoethyl)-$\underline{N}$-methylamino, $\underline{N}$-(3-dimethylaminopropyl)-$\underline{N}$-methylamino, 4-methylpiperazin-1-yl, 4-ethylpiperazin-1-yl, 4-methylhomopiperazin-1-yl or 4-methylpiperazin-1-ylmethyl;

n is 0;

q is 0; and

Q is 2-(pyrrolidin-1-yl)pyrid-4-yl, 2-(3-pyrrolin-1-yl)pyrid-4-yl, 2-piperidinopyrid-4yl, 2-morpholinopyrid-4-yl, 1-fluorenyl, dibenzofuran-4-yl, 3-acetamidophenyl or 3-(2-furyl)phenyl;

or a pharmaceutically-acceptable salt thereof.

A further especially preferred compound of the second aspect of the invention is an amide derivative of the Formula I wherein X is CH;

Y is CH or N;

R³ is chloro or methyl;

m is 1 and R¹ is $\underline{N}$-(3-dimethylaminopropyl)-$\underline{N}$-methylamino, 4-methylpiperazin-1-yl, 4-methylhomopiperazin-1-yl or 4-methylpiperazin-1-ylmethyl;

n is 0;

q is 0; and

Q is 2-morpholinopyrid-4yl;

or a pharmaceutically-acceptable salt thereof.

An amide derivative of the Formula I, or a pharmaceutically-acceptable salt or in-vivo-cleavable ester thereof, may be prepared by any process known to be applicable to the preparation of chemically-related compounds. Such processes, when used to prepare a novel amide derivative of the Formula I are provided as a further feature of the invention and are illustrated by the following representative process variants in which, unless otherwise stated, X, Y, R¹, R², R³, m, n, q and Q have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) A compound of the Formula I, or a pharmaceutically-acceptable salt or in-vivo-cleavable ester thereof, may be prepared by reacting an aniline of the Formula II

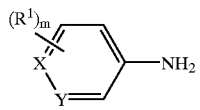

II with a benzoic acid of the Formula III, or an activated derivative thereof,

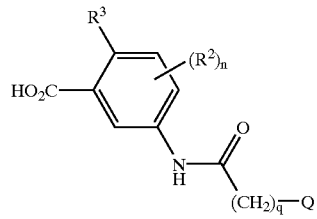

III under standard amide bond forming conditions, wherein variable groups are as defined hereinbefore and wherein any functional group is protected, if necessary and:

(i) removing any protecting groups;

(ii) optionally forming a pharmaceutically-acceptable salt or in-vivo-cleavable ester.

A suitable reactive derivative of a carboxylic acid of the Formula III is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid with a phenol such as pentafluorophenol, with an ester such as pentafluorophenyl trifluoroacetate or with an alcohol such as $\underline{N}$-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The standard amide bond forming conditions conveniently include the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene.

The reaction is also preferably carried out in a suitable inert solvent or diluent, for example methanol, ethanol, tetrahydrofuran, methylene chloride, 1,2-dimethoxyethane, $\underline{N},\underline{N}$-dimethylformamide, $\underline{N},\underline{N}$-dimethylacetamide, $\underline{N}$-methylpyrrolidin-2-one, dimethylsulphoxide or acetone, and at a temperature in the range, for example, 0 to 100° C., conveniently at or near ambient temperature.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

Typical standard amide bond forming conditions include activating the carboxy group, for example by treatment with a halo reagent (for example oxalyl chloride) to form an acyl halide in an organic solvent at ambient temperature and then reacting the activated compound with an aniline. Any functional groups are protected and deprotected as necessary. Conveniently a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and tert-butyldimethylsilyl); tri(lower alkyl)silyl lower alkyl groups (for example trimethylsilylethyl); and (2–6C)alkenyl groups (for example allyl and vinylethyl). Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkytsilyl (for example trimethylsilyl, tert-butyldimethylsilyl) and aryl lower alkyl (for example benzyl) groups.

Examples of amino protecting groups include formyl aralkyl groups (for example benzyl and substituted benzyl, p-methoxybenzyl, nitrobenzyl and 2,4-dimethoxybenzyl, and triphenylmethyl); di-p-anisylmethyl and furylmetlyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl; tri-alkylsiyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

The benzoic acid of the Formula III may be prepared by the cleavage of the corresponding ester thereof which, in turn, may be prepared by the reaction of an aniline of the Formula IV

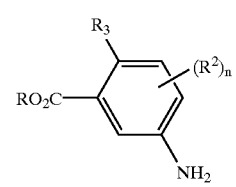

IV wherein R is, for example, lower alkyl or benzyl with a carboxylic acid of the Formula V, or an activated derivative thereof as defined hereinbefore, $$HO_2C-(CH_2)_q-Q \qquad\qquad V$$

under standard amide bond forming conditions as defined hereinbefore, wherein variable groups are as defined hereinbefore and wherein any functional group is protected if necessary.

(b) A compound of the Formula I, or a pharmaceutically-acceptable salt or in-vivo-cleavable ester thereof, may be prepared by reacting an aniline of the Formula VI

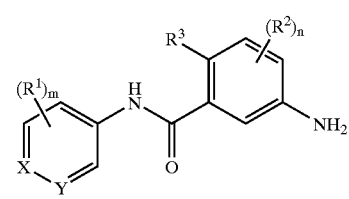

VI with a carboxylic acid of the Formula V, or a reactive derivative thereof as defined hereinbefore, $HO_2C—(CH_2)_q—Q$     V

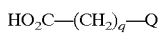

under standard amide bond forming conditions as defined hereinbefore, wherein variable groups are as defined hereinbefore and wherein any functional group is protected if necessary, and:

(i) removing any protecting groups; and
(ii) optionally forming a pharmaceutically-acceptable salt or in-vivo-cleavable ester.

The aniline of the Formula VI may be prepared by the reduction of the corresponding nitrobenzene compound of the Formula VII

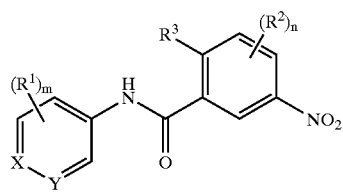

VII wherein variable groups are as defined hereinbefore and wherein any functional group is protected if necessary.

Typical reaction conditions for the reduction include the use of ammonium formate or hydrogen gas in the presence of a catalyst, for example a metallic catalyst such as palladium-on-carbon. Alternatively a dissolving metal reduction may be carried out, for example using iron in the presence of an acid, for example an inorganic or organic acid such as hydrochloric, hydrobromic, sulphuric or acetic acid. The reaction is conveniently carried out in the presence of an organic solvent (preferably a polar protic solvent) and preferably with heating, for example to about 60° C. Any functional groups are protected and deprotected as necessary.

The nitrobenzene compound of the Formula VII may be prepared by the reaction of the aniline of the Formula II

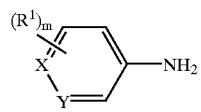

II with a carboxylic acid of the Formula VIII, or a reactive derivative thereof as defined hereinbefore,

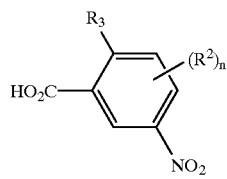

VIII under standard amide bond forming conditions as defined hereinbefore, wherein variable groups are as defined hereinbefore and wherein any functional group is protected if necessary.

(c) A compound of the Formula I wherein $R^1$ or a substituent on Q is (1–6C)alkoxy or substituted (1–6C)alkoxy, (1–6C) alkylthio, (1–6C)alkylamino, di-[(1–6C)alkyl]amino or substituted (1–6C)alkylamino may be prepared by the alkylation, conveniently in the presence of a suitable base as defined hereinbefore, of an amide derivative of the Formula I wherein $R^1$ or a substituent on Q is hydroxy, mercapto or amino as appropriate.

The reaction is preferably carried out in the presence of a suitable inert solvent or diluent, for example a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 150° C., preferably in the range 20 to 80° C.

A suitable alkylating agent is, for example, any agent known in the art for the alkylation of hydroxy to alkoxy or substituted alkoxy, or for the alkylation of mercapto to alkylthio, or for the alkylation of amino to alkylamino or substituted alkylamino, for example an alkyl or substituted alkyl halide, for example a (1–6C)alkyl chloride, bromide or iodide or a substituted (1–6C)alkyl chloride, bromide or iodide, in the presence of a suitable base as defined hereinbefore, in a suitable inert solvent or diluent as defined hereinbefore and at a temperature in the range, for example, 10 to 140° C., conveniently at or near ambient temperature.

(d) A compound of the Formula I wherein a substituent on Q is amino, (1–6C)alkylamino, di-[(1–6C)alkyl]amino, substituted (1–6C)alkylamino, substituted N-(1–6C)alkyl-(2–6C)alkylamino or a N-linked heterocyclyl group may be prepared by the reaction, conveniently in the presence of a suitable base as defined hereinbefore, of an amide derivative of the Formula I wherein a substituent on Q is a suitable leaving group with an appropriate amine.

A suitable leaving group is, for example, a halogeno group such as fluoro, chloro or bromo, a (1–6C) alkanesulphonyloxy group such as methanesulphonyloxy or an arylsulphonyloxy group such as 4-toluenesulphonyloxy.

The reaction is conveniently carried out in the presence of a suitable inert diluent or carrier as defined hereinbefore and at a temperature in the range, for example, 20 to 200° C., conveniently in the range 75 to 150° C.

(e) A compound of the Formula I wherein $R^1$ or a substituent on Q is (1–6C)alkanoylamino or substituted (2–6C) alkanoylamino may be prepared by the acylation of a compound of the Formula I wherein $R^1$ or a substituent on Q is amino.

A suitable acylating agent is, for example, any agent known in the art for the acylation of amino to acylamino, for example an acyl halide, for example a (1–6C)alkanoyl chloride or bromide, conveniently in the presence of a suitable base, as defined hereinbefore, an alkanoic acid anhydride or mixed anhydride, for example a (1–6C) alkanoic acid anhydride such as acetic anhydride or the mixed anhydride formed by the reaction of an alkanoic acid and a (1–6C)alkoxycarbonyl halide, for example a (1–6C) alkoxycarbonyl chloride, in the presence of a suitable base as defined hereinbefore. In general the acylation is carried out in a suitable inert solvent or diluent as defined hereinbefore and at a temperature, in the range, for example, –30 to 120° C., conveniently at or near ambient temperature.

(f) A compound of the Formula I wherein $R^1$ or a substituent on Q is (1–6C)alkanesulphonylamino may be prepared by the reaction of a compound of the Formula I wherein $R^1$ or a substituent on Q is amino with a (1–6C)alkanesulphonic acid, or an activated derivative thereof.

A suitable activated derivative of a (1–6C) alkanesulphonic acid is, for example, an alkanesulphonyl halide, for example an alkanesulphonyl chloride formed by the reaction of the sulphonic acid and an inorganic acid chloride, for example thionyl chloride. The reaction is preferably carried out in the presence of a suitable base as defined hereinbefore, particularly pyridine, and in a suitable inert solvent or diluent as defined hereinbefore, particularly methylene chloride.

(g) A compound of the Formula I wherein $R^1$ or a substituent on Q is carboxy, carboxy-(1–6C)alkyl, carboxy-(1–6C) alkoxy, carboxy-(1–6C)alkylamino, N-(1–6C)alkyl-carboxy-(1–6C)alkylamino or carboxy-(2–6C) alkanoylamino may be prepared by the cleavage of a compound of the Formula I wherein $R^1$ or a substituent on Q is (1–6C)alkoxycarbonyl, (1–6C)alkoxycarbonyl-(1–6C)alkyl, (1–6C)alkoxycarbonyl-(1–6C)alkoxy, (1–6C) alkoxycarbonyl-(1–6C)alkylamino, N-(1–6C)alkyl-(1–6C) alkoxycarbonyl-(1–6C)alkylamino or (1–6C) alkoxycarbonyl-(2–6C)alkanoylamino as appropriate.

The cleavage reaction may conveniently be carried out by any of the many procedures known in the art for such a transformation. The reaction may be carried out, for example, by hydrolysis under acidic or basic conditions. A suitable base is, for example, an alkali metal, alkaline earth metal or ammonium carbonate or hydroxide, for example sodium carbonate, potassium carbonate, sodium hydroxide, potassium hydroxide or ammonium hydroxide. The reaction is preferably carried out in the presence of water and a suitable solvent or diluent such as methanol or ethanol. The reaction is conveniently carried out at a temperature in the range 10 to 150° C., preferably at or near ambient temperature.

(h) A compound of the Formula I wherein $R^1$ is amino-(1–6C)alkyl, (1–6C)alkylamino-(1–6C)alkyl, di-[(1–6C) alkyl]amino-(1–6C)alkyl or a heterocyclyl-(1–6C)alkyl group may be prepared by the reaction, conveniently in the presence of a suitable base as defined hereinbefore, of a compound of the Formula IX

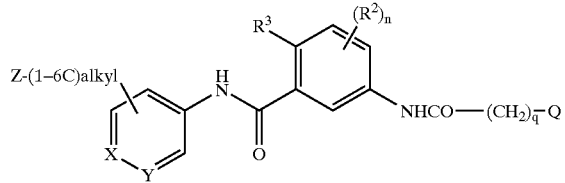

wherein X, Y, $R^2$, $R^3$, n, q and Q have any of the meanings defined hereinbefore and Z is a suitable leaving group with an appropriate amine or heterocycle.

A suitable leaving group Z is, for example, a halogeno group such as fluoro, chloro or bromo, a (1–6C) alkanesulphonyloxy group such as methanesulphonyloxy or an arylsulphonyloxy group such as 4-toluenesulphonyloxy.

The reaction is conveniently carried out in the presence of a suitable inert diluent or carrier as defined hereinbefore and at a temperature in the range, for example, 20 to 200° C., conveniently in the range 50 to 150° C.

The following biological assays and Examples serve to illustrate the present invention.
Biological Assays
The following assays can be used to measure the p38 kinase-inhibitory, the TNF-inhibitory and anti-arthritic effects of the compounds of the present invention.
In Vitro Enzyme Assay
The ability of compounds of the invention to inhibit the enzyme p38 kinase was assessed. Activity of test compounds against each of the p38α and p38β isoforms of the enzyme was determined.

Human recombinant MKK6 (GenBank Accesion Number G1209672) was isolated from Image clone 45578 (*Genomics*, 1996, 33, 151) and utilised to produce protein in the form of a GST fusion protein in a pGEX vector using analogous procedures to those disclosed by J. Han et al., *Journal of Biological Chemistry*, 1996, 271, 2886–2891, p38α (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no 6525-1) using a Gibco superscript cDNA synthesis kit] respectively using otigonucleotides designed for the 5' and 3' ends of the human p38α and p38β genes using analogous procedures to those described by J. Han et al., *Biochimica et Biophysica Acta*, 1995, 1265, 224–227 and Y. Jiang et al., *Journal of Biological Chemistry*, 1996, 271, 17920–17926.

Both p38 protein isoforms were expressed in *e coli* in PET vectors. Human recombinant p38α and p38β isoforms were produced as 5' c-myc, 6His tagged proteins. Both MKK6 and the p38 proteins were purified using standard protocols: the GST MKK6 was purified using a glutathione sepharose column and the p38 proteins were purified using nickel chelate columns.

The p38 enzymes were activated prior to use by incubation with MKK6 for 3 hours at 30° C. The unactivated coli-expressed MKK6 retained sufficient activity to fully activate both isoforms of p38. The activation incubate comprised p38α (10 μl of 10 μmg/ml) or p38β (10 μl of 5 mg/ml) together with MKK6 (10 μl of 1 mg/ml), 'Kinase buffer' [100 μl; pH 7.4 buffer comprising Tris (50 mM), EGTA (0.1 mM), sodium orthovanadate (0.1 mM) and β-mercaptoethanol (0.1%)] and MgATP (30 μl of 50 mM Mg(OCOCH$_3$)$_2$ and 0.5 mM ATP). This produced enough activated p38 enzyme for 3 Microtiter plates.

Test compounds were solubilised in DMSO and 10 μl of a 1:10 diluted sample in 'Kinase Buffer' was added to a well in a Microtiter plate. For single dose testing, the compounds were tested at 10 μM, 'Kinase Assay Mix' [30 μl; comprising Myelin Basic Protein (Gibco BRL cat. no. 1322B-010; 1 ml of a 3.33 mg/ml solution in water), activated p38 enzyme (50 μl) and 'Kinase Buffer' (2 ml)] was then added followed by 'Labelled ATP' [10 μl; comprising 50 μM ATP, 0.1 μCi $^{33}$P ATP (Amersham International cat. no. BF1000) and 50 mM Mg(OCOCH$_3$)$_2$]. The plates were incubated at room temperature with gentle agitation. Plates containing p38α were incubated for 90 min and plates containing p38β were incubated for 45 min. Incubation was stopped by the addition of 50 μl of 20% trichloroacetic acid (TCA). The precipitated protein was phosphorylated by p38 kinase and test compounds were assessed for their ability to inhibit this phosphorylation. The plates were filtered using a Canberra Packard Unifilter and washed with 2% TCA, dried overnight and counted on a Top Count scintillation counter.

Test compounds were tested initially at a single dose and active compounds were retested to allow $IC_{50}$ values to be determined.

In Vitro Cell-Based Assays
(i) PBMC

The ability of compounds of this invention to inhibit TNFα production was assessed by using human peripheral blood mononuclear cells which synthesise and secrete TNFα when stimulated with lipopolysaccharide.

Peripheral blood mononuclear cells (PBMC) were isolated from heparinised (10 units/ml heparin) human blood by density centrifugation (Lymphoprep™; Nycomed). Mononuclear cells were resuspended in culture medium [RPMI 1640 medium (Gibco) supplemented with 50 units/ml penicillin, 50 µg/ml streptomycin, 2 mM glutamine and 1% heat-inactivated human AB serum (Sigma H-1513)]. Compounds were solubilised in DMSO at a concentration of 50 mM, diluted 1:100 in culture medium and subsequently serial dilutions were made in culture medium containing 1% DMSO. PBMCs ($2.4 \times 10^5$ cells in 160 µl culture medium) were incubated with 20 µl of varying concentrations of test compound (triplicate cultures) or 20 µl culture medium containing 1% DMSO (control wells) for 30 minutes at 37° C. in a humidified (5% $CO_2$/95% air) incubator (Falcon 3072; 96 well flat-bottom tissue culture plates), 20 µl lipopolysaccharide [LPS $E.\ Coli$ 0111:B4 (Sigma L-4130), final concentration 10 µg/ml] solubilised in culture medium was added to appropriate wells, 20 µl culture medium was added to "medium alone" control wells. Six "LPS alone" and four "medium alone" controls were included on each 96 well plate. Varying concentrations of a known TNFα inhibitor were included in each test, i.e. an inhibitor of the PDE Type IV enzyme (for example see Semmler, J. Wachtel. H and Endres, S., $Int.\ J.\ Immunopharmac.$ (1993), 15(3), 409–413) or an inhibitor of pro TNFα convertase (for example, see McGeehan, G. M. et al. $Nature$ (1994) 370, 558–561). Plates were incubated for 7 hours at 37° C. (humidified incubator) after which 100 µl of the supernatant was removed from each well and stored at −70° C. (96 well round-bottom plates;1 Corning 25850). TNFα levels were determined in each sample using a human TNFα ELISA (see WO92/10190 and $Current\ Protocols\ in\ Molecular\ Biology$, vol 2 by Frederick M. Ausbel et al., John Wiley and Sons Inc.).

% inhibition=(LPS alone−medium alone)−(test concentration−medium alone)/(LPS alone−medium alone)×100

(ii) Human Whole Blood

The ability of the compounds of this invention to inhibit TNFα production was also assessed in a human whole blood assay. Human whole blood secretes TNFα when stimulated with LPS. This property of blood forms the basis of an assay which is used as a secondary test for compounds which profile as active in the PBMC test.

Heparinised (10 units/ml) human blood was obtained from volunteers. 160 µl whole blood were added to 96 well round-bottom plates (Corning 25850). Compounds were solubilised and serially diluted in RPMI 1640 medium (Gibco) supplemented with 50 units/ml penicillin, 50 µg/ml streptomycin and 2 mM glutamine, as detailed above. 20 µl of each test concentration was added to appropriate wells (triplicate cultures). 20 µl of RPMI 1640 medium supplemented with antibiotics and glutamine was added to control wells. Plates were incubated for 30 minutes at 37° C. (humidified incubator), prior to addition of 20 µl LPS (final concentration 10 µg/ml). RPMI 1640 medium was added to control wells. Six "LPS alone" and four "medium alone" controls were included on each plate. A known TNFα synthesis/secretion inhibitor was included in each test. Plates were incubated for 6 hours at 37° C. (humidified incubator). Plates were centrifuged (2000 rpm for 10 minutes) and 100 µl plasma removed and stored at −70° C. (Corning 25850 plates). TNFα levels were measured by ELISA (see WO92/10190 and $Current\ Protocols\ in\ Molecular\ Biology$, vol 2 by Frederick M. Ausbel et al., John Wiley and Sons Inc.). The paired antibodies that were used in the ELIZA were obtained from R&D Systems (catalogue nos. MAB610 anti-human TNFα coating antibody, BAF210 biotinylated anti-human TNFα detect antibody).

Ex Vivo/In Vivo Assessment

The ability of the compounds of this invention as ex vivo TNFα inhibitors were assessed in the rat or mouse. Briefly, groups of male Wistar Alderley Park (AP) rats (180–210 g) were dosed with compound (6 rats) or drug vehicle (10 rats) by the appropriate route, for example peroral (p.o.), intraperitoneal (i.p.) or subcutaneous (s.c.). Ninety minutes later rats were sacrificed using a rising concentration of $CO_2$ and bled out via the posterior vena cavae into 5 Units of sodium heparin/ml blood. Blood samples were immediately placed on ice and centrifuged at 2000 rpm for 10 min at 4° C. and the harvested plasmas frozen at −20° C. for subsequent assay of their effect on TNFα production by LPS-stimulated human blood. The rat plasma samples were thawed and 175 µl of each sample was added to a set format pattern in a 96 well round bottom plate (Corning 25850). 50 µl of heparinized human blood was then added to each well, mixed and the plate was incubated for 30 min at 37° C. (humidified incubator). LPS (25 µl; final concentration 10 µg/ml) was added to the wells and incubation continued for a further 5.5 hours. Control wells were incubated with 25 µl of medium alone. Plates were then centrifuged for 10 min at 2000 rpm and 200 µl of the supernatants were transferred to a 96 well plate and frozen at −20° C. for subsequent analysis of TNF concentration by ELISA.

Data analysis by dedicated software calculates for each compound/dose:

% inhibition of TNFα=Mean TNFα (Controls)−Mean TNFα (Treated)/Mean TNFα (Controls)×100

Alternatively, mice could be used instead of rats in the above procedure.

Test as Anti-arthritic Agent

Activity of a compound as an anti-arthritic agent was tested as follows. Acid soluble native type II collagen was shown by Trentham et al. [1] to be arthritogenic in rats; it caused polyarthritis when administered in Freunds incomplete adjuvant. This is now known as collagen-induced arthritis (CIA) and similar conditions can be induced in mice and primates. Recent studies have shown that anti-TNF monoclonal antibodies [2] and TNF receptor-IgG fusion proteins [3] ameliorate established CIA indicating that TNF plays a key role in the pathophsiology of CIA. Moreover, the remarkable efficacy reported for anti-TNF monoclonal antibodies in recent rheumatoid arthritis clinical trials indicates that TNF plays a major role in this chronic inflammatory disease. Thus CIA in DBA/1 mice as described in references 2 and 3 is a tertiary model which can be used to demonstrate the anti-arthritic activity of a compound. Also see reference 4.

1. Trentham, D. E. et al., (1977) *J. Exp. Med.*, 146, 857.
2. Williams, R. O. et al., (1992) *Proc. Natl. Acad. Sci.*, 89, 9784.
3. Williams, R. O. et al., (1995) *Immunology*, 84, 433.
4. Badger, M. B. et al., (1996) *The Journal of Pharmacology and Experimental Therapeutics*, 279, 1453–1461.

Although the pharmacological properties of the compounds of the Formula I vary with structural chance as expected, in general a compound of the Formula I gives over 30% inhibition of p38α and/or p38β at concentrations up to 10 μM. No physiologically unacceptable toxicity was observed at the effective dose for compounds tested of the present invention.

By way of example, the compound N-{6-[N-(3-dimethylaminopropyl)-N-methylamino]pyrid-3-yl}-2-chloro-5-(2-morpholinopyrid-4-ylcarbonylamino) benzamide has an $IC_{50}$ of approximately 0.05 μM against p38α and an $IC_{50}$ of approximately 5 μM in the Human Whole Blood test.

According to a further aspect of the invention there is provided a pharmaceutical composition which comprises an amide derivative of the Formula I, or a pharmaceutically-acceptable or in-vivo-cleavable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

According to a further aspect of the invention there is provided an amide derivative of the Formula I, or a pharmaceutically-acceptable salt or in-vivo-cleavable ester thereof, as defined hereinbefore for use in a method of treatment of the human or animal body by therapy.

According to a further aspect of the invention there is provided the use of an amide derivative of the Formula I, or a pharmaceutically-acceptable salt or in-vivo-cleavable ester thereof, as defined hereinbefore in the manufacture of a medicament for use in the treatment of diseases or medical conditions mediated by cytokines.

In a further aspect the present invention provides a method of treating diseases or medical conditions mediated by cytokines which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of a compound of the Formula I or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in inhibiting TNF.

In a further aspect the present invention provides a method of inhibiting TNF which comprises administering to a warm-blooded animal an effective amount of a compound of the Formula I, or a pharmaceutically-acceptable salt or in vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of rheumatoid arthritis, asthma, irritable bowel disease, multiple sclerosis, AIDS, septic shock, ischaemic heart disease or psoriasis.

In a further aspect the present invention provides a method of treating rheumatoid arthritis, asthma, irritable bowel disease, multiple sclerosis, AIDS, septic shock, ischaemic heart disease or psoriasis which comprises administering to a warm-blooded animal an effective amount of a compound of the Formula I, or a pharmaceutically-acceptable salt or in-vivo-cleavable ester thereof.

The compounds of this invention may be used in combination with other drugs and therapies used in the treatment of disease states which would benefit from the inhibition of cytokines, in particular TNF and IL-1. For example, the compounds of the Formula I could be used in combination with drugs and therapies used in the treatment of rheumatoid arthritis, asthma, irritable bowel disease, multiple sclerosis, AIDS, septic shock, ischaemic heart disease, psoriasis and the other disease states mentioned earlier in this specification.

For example, by virtue of their ability to inhibit cytokines, the compounds of the Formula I are of value in the treatment of certain inflammatory and non inflammatory diseases which are currently treated with a cyclooxygenase-inhibitory-non-steroidal anti-inflammatory drug (NSAID) such as indomethacin, ketorolac, acetylsalicyclic acid, ibuprofen, sulindac, tolmetin and piroxicam. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt or in-vivo-cleavable ester thereof, in conjunction or admixture with a cyclooxygenase inhibitory non-steroidal anti-inflammatory agent, and a pharmaceutically-acceptable diluent or carrier.

The compounds of the invention may also be used with anti-inflammatory agents such as an inhibitor of the enzyme 5-lipoxygenase.

The compounds of the Formula I may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of the Formula I may be be used in the treatment of asthma in combination with antiasthmatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of cytokines. Thus, they are useful as pharmacological standards for use in the development of new biological tests and in the search for new pharmacological agents.

The invention will now be illustrated in the following non-limiting Examples in which, unless otherwise stated:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields are given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; t, triplet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:
DMF N,N-dimethylformamide
DMSO dimethylsulphoxide
THF tetrahydrofuran.

EXAMPLE 1

N-(4-propylphenyl)-5-(4-cyanobenzamido)-2-methylbenzamide 4-n-Propylaniline (0.11 g) was added to a stirred suspension of 5-(4-cyanobenzamido)-2-methylbenzoyl chloride (0.224 g), triethylamine (0.21 ml) and methylene chloride (5 ml) and the resultant mixture was stirred at ambient temperature for 16 hours. The mixture was filtered and the filtrate was evaporated. The residue was purified by column chromatography on silica using increasingly polar mixtures of methylene chloride and methanol as eluent, There was thus obtained the title compound (0.049 g); NMR Spectrum: (DMSOd$_6$) 0.87 (t, 3H), 1.56 (m, 2H), 2.33 (s, 3H), 2.48 (m, 2H), 7.13 (d, 2H), 7.28 (d, 1H), 7.63 (m, 2H), 7.83 (m, 3H), 8.01 (d, 1H), 8.1 (m, 2H); Mass Spectrum: M+H$^+$ 398.

The 5-(4-cyanobenzamido)-2-methylbenzoyl chloride used as a starting material was prepared as follows:

4-Cyanobenzoyl chloride (4.50 g) was added to a stirred suspension of methyl 5-amino-2-methylbenzoate (*J. Med. Chem.*, 1991, 34, 2176–2186; 3 g), triethylamine (2.54 ml) and methylene chloride (100 ml) and the resultant mixture was stirred at ambient temperature for 16 hours. The mixture was acidified by the addition of 1N aqueous hydrochloric acid solution and the mixture was stirred at ambient temperature for 30 minutes. The resultant solid was isolated and dried under vacuum at 40° C. to give methyl 5-(4-cyanobenzamido)-2-methylbenzoate (5.32 g); NMR Spectrum: (DMSOd$_6$) 2.47 (s, 3H), 3.83 (s, 3H), 7.31 (d, 1H), 7.88 (d, 1H), 8.0 (d, 2H), 8.1 (d, 2H), 8.27 (s,1H), 10.57 (s, 1H); Mass Spectrum: M+H$^+$ 295.

A mixture of a portion (3 g) of the material so obtained, 2N aqueous sodium hydroxide solution (20.4 ml), water (10 ml) and methanol (80 ml) was stirred at ambient temperature for 16 hours. And then heated to 50° C. for 5 hours. The resultant solution was evaporated and the residue was partitioned between ethyl acetate and water. The aqueous phase was acidified to pH5 by the addition of 1N aqueous hydrochloric acid solution and the resultant solid was isolated and dried under vacuum at 40° C. There was thus obtained 5-(4-cyanobenzamido)-2-methylbenzoic acid (1.79 g); NMR Spectrum: (DMSOd$_6$) 2.45 (s, 3H), 7.24 (d, 1H), 7.84 (m, 1H), 8.02 (m, 4H), 8.26 (s, 1H), 10.41 (d, 1H); Mass Spectrum: M–H$^-$ 279.

Oxalyl chloride (0.104 g) was added dropwise to a stirred mixture of 5-(4-cyanobenzamido)-2-methylbenzoic acid (0.21 g), DMF (a few drops) and methylene chloride (10 ml) which had been cooled to 0° C. The mixture was allowed to warm to ambient temperature and was stirred for 4 hours. The mixture was evaporated to give the required starting material which was used without further purification.

EXAMPLE 2

Using an analogous procedure to that described in Example 1, the appropriate benzoyl chloride was reacted with the appropriate aniline to give the compounds described in Table I,

TABLE I

| No. | (R$^1$)$_m$ | R$^3$ | Q | Note |
|---|---|---|---|---|
| 1 | 4-propyl | methyl | phenyl | a |
| 2 | 3,4-dimethoxy | methyl | phenyl | b |
| 3 | 3,4-dimethoxy | methyl | 4-cyanophenyl | c |

Notes
a) The product gave the following data: NMRSpectrum: (DMSOd$_6$) 0.87(t, 3H), 1.52–1.56(m, 2H), 2.32(s, 3H), 2.48–2.53(m, 2H), 7.13(d, 2H), 7.26 (d, 1H), 7.51–7.63(m, 5H), 7.8(d, 1H), 7.86(s, 1H), 7.95(d, 2H), 10.21(s, 1H), 10.29(s, 1H); MassSpectrum: M + H$^+$ 373.

The 5-benzamido-2-methylbenzoyl chloride used as a starting material was prepared from methyl 5-amino-2-methylbenzoate and benzoyl chloride using analogous procedures to those described in the portion of Example 1 which is concerned with the preparation of starting materials. There were thus obtained in turn: methyl 5-benzamido-2-methylbenzoate NMR Spectrum: (DMSOd$_6$) 2.43 (s, 3H), 3.83 (s, 3H), 7.29 (d, 1H), 7.49–7.61 (m, 3H), 7.88 (d, 1H), 7.95 (d, 2H), 8.29 (s, 1H), 10.33 (s, 1H); Mass Spectrum: M+H$^+$ 270; 5-benzamido-2-methylbenzoate NMR Spectrum: (DMSOd$_6$) 2.43 (s, 3H), 7.24 (d, 1H), 7.44–7.6 (m, 3H), 7.84 (d, 1H), 7.94 (d, 2H), 8.25 (s, 1H), 10.39 (s, 1H), 12.80 (s, 1H); Mass Spectrum: M+H$^+$ 254: and 5-benzamido-2-methylbenzoyl chloride which was used without further purification.

b) After the reaction mixture had been stirred at ambient temperature for 16 hours, the mixture was filtered and the filtrate was washed in turn with a 1N aqueous hydrochloric acid solution and a saturated aqueous sodium bicarbonate solution. The organic phase was evaporated and the residue was triturated under a mixture of isohexane and ethyl acetate. The resultant solid was isolated, washed with diethyl ether and dried. The product so obtained gave the following data: NMR Spectrum: (DMSOd$_6$) 2.33 (s, 3H), 3.72 (s, 6H), 6,9 (d, 1H), 7.25 (d, 2H), 7.43–7.58 (m, 4H), 7.78 (d, 1H), 7.87 (s, 1H), 7.95 (d, 2H), 10.13 (s, 1H), 10.29 (s, 1H); Mass Spectrum: M+H$^+$ 391.

c) After the reaction mixture had been stirred at ambient temperature for 16 hours, the mixture was filtered and the filtrate was washed in turn with a 1N aqueous hydrochloric acid solution and a saturated aqueous sodium bicarbonate solution. The organic phase was evaporated and the residue was triturated under a mixture of isohexane and ethyl acetate. The resultant solid was isolated, washed with diethyl ether and dried. The product so obtained gave the following data: Mass Spectrum: M+H$^+$ 416.

EXAMPLE 3

N-[3-(4-methylpiperazin-1-ylmethyl)phenyl]-2-methyl-5-(2-morpholinopyrid-4-ylcarbonylamino)benzamide Using an analogous procedure to that described in Example 1, 2-morpholinopyridine-4-carbonyl chloride was reacted with N-[3-(4-methylpiperazin-1-ylmethyl)phenyl]-5-amino-2-methylbenzamide. The residue was purified by column chromatography on an ion exchange column (isolute SCX column from International Sorbent Technology Limited, Hengoed, Mid-Glamorgan, UK) using initially methanol and then a 99:1 mixture of methanol and a saturated aqueous ammonium hydroxide solution as eluent. There was thus obtained the title compound in 27% yield; Mass Spectrum: M+H$^+$ 529.

The 2-morpholinopyridine-4-carbonyl chloride used as a starting material was prepared as follows:

2-Chloropyridine-4-carbonyl chloride (11.2 g) was added to a stirred mixture of potassium tert-butoxide (7.15 g) and THF (50 ml) which had been cooled to 0° C. The mixture was allowed to warm to ambient temperature and was stirred for 16 hours. The mixture was evaporated and the residue was partitioned between ethyl acetate and water. The organic phase was washed with a saturated aqueous sodium bicarbonate solution, dried (MgSO$_4$) and evaporated. There was thus obtained tert-butyl 2chloropyridine-4-carboxylate (10.5 g); NMR Spectrum: (CDCl$_3$) 1.6 (s, 9H), 7.72 (d, 1H), 7.82 (s, 1H), 8.51 (d, 1H).

After repetition of the previous reaction, a mixture of the pyridine-4-carboxylate so produced (18.3 g) and morpholine (30 ml) was stirred and heated to 100° C. for 40 hours. The mixture was poured into water and extracted with methylene chloride. The organic phase was evaporated and the residue was purified by column chromatography on silica using initially a 5:1 mixture of isohexane and ethyl acetate and then a 10:3 mixture of the same solvents as eluent. There was thus obtained tert-butyl 2-morpholinopyridine-4-carboxylate (15 g); NMR Spectrum: (DMSOd$_6$) 1.52 (s, 9H), 3.46–3.55 (m, 4H) 3.62–3.7 (m, 4H) 7.09 (d, 1H), 7.13 (s, 1H), 8.24 (d, 1H).

A mixture of the material so obtained, water (10 ml) and trifluoroacetic acid (90 ml) was stirred at ambient temperature for 3 hours. The mixture was evaporated and the residue was triturated under a mixture of isohexane and ethyl acetate. The resultant solid was isolated, washed with ethyl acetate and dried to give 2-morpholinopyridine-4-carboxylic acid (13.2 g); NMR Spectrum: (DMSOd$_6$) 3.46–3.51 (m, 4H), 3.62–3.7 (m, 4H), 7.07 (d, 1H), 7.25 (s, 1H), 8.24 (d, 1H).

The material so obtained was reacted with oxalyl chloride using an analogous procedure to that described in the last paragraph of the portion of Example 1 which is concerned with the preparation of starting materials. There was thus obtained 2-morpholinopyridine-4-carbonyl chloride which was used without further purification.

The N-[3-(4-methylpiperazin-1-ylmethyl)phenyl]-5-amino-2-methylbenzamide used as a starting material was prepared as follows:

A mixture of 3-nitrobenzyl chloride (1 g) and N-methylpiperazine (3 ml) was stirred and heated to 100° C. for 4 hours. The mixture was cooled to ambient temperature and partitioned between methylene chloride and water. The organic phase was evaporated to give 3-(4-methylpiperazin-1-ylmethyl)nitrobenzene (1.05 g); NMR Spectrum: (DMSOd$_6$) 2.14 (s, 3H), 2.31–2.38 (m, 8H), 3.57 (s, 2H), 7.6 (t, 1H), 7.54 (d, 1H), 8.07–8.13 (m, 2H).

Iron powder (2.47 g) was added to a stirred suspension of the material so obtained in a mixture of ethanol (30 ml), water (2 ml) and acetic acid (0.5 ml). The mixture was stirred and heated to reflux for 4 hours. The mixture was cooled to ambient temperature. Water (30 ml) was added and the resultant mixture was basified by the addition of sodium carbonate. The mixture was filtered and the filtrate was evaporated. The residue was triturated under water. The resultant solid was isolated and dried under vacuum at 40° C. There was thus obtained 3-(4-methylpiperazin-1-ylmethyl)aniline (0.51 g); NMR Spectrum: (DMSOd$_6$) 2.11 (s, 3H), 2.24–2.36 (m, 8H), 3.28 (s, 2H), 4.92 (s, 2H), 6.37–6.41 (m, 2H), 6.49 (s, 1H), 7.9 (t, 1H).

Oxalyl chloride (0.31 g) was added dropwise to a stirred mixture of 2-methyl-5-nitrobenzoic acid (0.4 g), DMF (a few drops) and methylene chloride (25 ml) which had been cooled to 0° C. The mixture was allowed to warm to ambient temperature and was stirred for five hours. The mixture was evaporated to give 2-methyl-5-nitrobenzoyl chloride which was dissolved in methylene chloride (10 ml) and added dropwise to a stirred mixture of 3-(4-methylpiperazin-1-ylmethyl)aniline (0.44 g), triethylamine (0.49 g) and methylene chloride (10 ml). The mixture was stirred at ambient temperature for 16 hours. The mixture was washed with a saturated aqueous sodium bicarbonate solution. The organic phase was evaporated and the residue was purified by column chromatography on an isolute SCX ion exchange column using initially methanol and then a 99:1 mixture of methanol and a saturated aqueous ammonium hydroxide solution as eluent. There was thus obtained N-[3-(4-methylpiperazin-1-ylmethyl)phenyl]-2-methyl-5-nitrobenzamide(0.46 g); Mass Spectrum: M+H$^+$ 369.

A mixture of the 5-nitrobenzamide so obtained, iron powder (2.79 g), water (1 ml), acetic acid (0.25 ml) and ethanol (15 ml) was stirred and heated to reflux for 5 hours. The mixture was cooled to ambient temperature. Water (50 ml) was added and the mixture was basified by the addition of sodium carbonate. The resultant mixture was filtered and the filtrate was evaporated. The residue was partitioned between methylene chloride and water. The organic phase was evaporated and the residue was purified by column chromatography on an isolute SCX ion exchange column using initially methanol and then a 99:1 mixture of methanol and a saturated aqueous ammonium hydroxide solution as eluent. There was thus obtained N-[3-(4-methylpiperazin-1-ylmethyl)phenyl]-5-amino-2-methylbenzamide (0.194 g); NMR Spectrum: (CDCl$_3$) 2.28 (s, 3H), 2.37 (s, 3H), 2.42–2.58 (m, 8H), 3.5 (s, 2H)) 3.64 (broad s, 2H), 5.29 (s, 1H), 6.67–6.81 (m, 2H), 7.02 (t, 1H), 7.10 (d, 1H), 7.3–7.6 (m, 1H); Mass Spectrum: M+H$^+$ 339.

EXAMPLE 4

N-[6-(4-ethylpiperazin-1-yl)pyrid-3-yl]-2-chloro-5-(2-morpholinopyrid-4-ylcarbonylamino)benzamide 2-Chloro-5-(2-morpholinopyrid-4-ylcarbonylamino) benzoic acid (0.162 g) was added to a stirred mixture of 5-amino-2-(4-ethylpiperazin-1-yl)pyridine (0.093 g), diisopropylethylamine (0.232 g), 2-(7-azabenzotriazol-1-yl)-1,1,3,3-tetramethyluronium hexafluorophosphate(V) (0.176 g) and DMF (10 ml) and the mixture was stirred at ambient temperature for 16 hours. The mixture was partitioned between ethyl acetate and water. The organic phase was washed with a saturated aqueous sodium bicarbonate solution and evaporated. The residue was triturated under a mixture of isohexane and ethyl acetate. The resultant solid was isolated and dried under vacuum at 40° C. to give the title compound (0.071 g); NMR Spectrum: (DMSOd$_6$) 1.02 (t, 3H), 2.34 (m, 2H), 2.4–2.46 (m, 4H), 3.38–3.42 (m, 4H), 3.5–3.53 (m, 4H), 3.69–3.71 (m, 4H), 6.82 (d, 1H), 7.08 (d, 2H), 7.22 (s, 1H), 7.62 (d, 1H), 7.82–7.98 (m, 3H), 8.28 (d, 1H), 8.39 (s, 1H); Mass Spectrum: M+H$^+$ 550 and 552.

The 2-chloro-5-(2-morpholinopyrid-4-ylcarbonylamino) benzoic acid used as a starting material was prepared as follows:

Using an analogous procedure to that described in the last paragraph of the portion of Example 3 which is concerned with the preparation of starting materials, methyl 2-chloro-5-nitrobenzoate was reduced to give methyl 5-amino-2-chlorobenzoate in 38% yield; NMR Spectrum: (DMSOd$_6$) 3.79 (s, 3H), 5.46 (s, 2H), 6.66 (d, 1H), 6.97 (s, 1H), 7.1 (d, 1H).

Using an analogous procedure to that described in Example 1, 2-morpholinopyridine-4-carbonyl chloride was reacted with methyl 5-amino-2-chlorobenzoate. The reaction product was triturated under a mixture of isohexane and ethyl acetate. The resultant solid was isolated and washed with diethyl ether. There was thus obtained methyl 2-chloro-5-(2-morpholinopyrid-4-ylcarbonylamino)benzoate in 63% yield; NMR Spectrum: (DMSOd$_6$) 3.49–3.53 (m, 4H), 3.69–3.72 (m, 4H), 3.86 (s, 3H), 7.09 (d, 1H), 7.23 (s, 1H), 7.56 (d, 1H), 7.96 (d, 1H), 8.25–8.28 (m, 2H), 10.55 (s, 1H); Mass Spectrum: M+H$^+$ 376 and 378.

A mixture of the methyl benzoate so obtained (3 g), 2N aqueous sodium hydroxide solution (16 ml), water (25 ml) and methanol (100 ml) was stirred at ambient temperature for 16 hours. The resultant solution was evaporated and the residue was acidified to pH1 by the addition of 1N aqueous hydrochloric acid solution. Water (1 ml) and methanol (1 ml) were added and the mixture was stirred for 1 hour. The resultant solid was isolated and dried under vacuum at 40° C. to give the required starting material (2.83 g); NMR Spectrum: (DMSOd$_6$) 3.62–3.74 (m, 8H), 7.21 (d, 1H), 7.53 (d, 1H), 7.63 (s, 1H), 8.01 (d, 1H), 8.21 (d, 1H), 8.28 (s, 1H), 10.98 (s, 1H); Mass Spectrum: M–H$^-$ 360 and 362.

The 5-amino-2-(4-ethylpiperazin-1-yl)pyridine used as a starting material was prepared as follows:

A mixture of 2-chloro-5-nitropyridine (1 g) and N-ethylpiperazine (4 ml) was stirred and heated to 100° C. for 16 hours. The mixture was cooled to ambient temperature and poured in water. The resultant solid was isolated, washed in turn with water and with diethyl ether and dried under vacuum at 40° C. There was thus obtained 2-(4-ethylpiperazin-1-yl)-5-nitropyridine (0.22 g); NMR Spectrum: (DMSOd$_6$) 1.01 (t, 3H), 2.33–2.41 (m, 2H), 2.42–2.44 (m, 4H), 3.71–3.75 (m, 4H), 6.91 (d, 1H), 8.17 (d, 1H), 8.92 (s, 1H).

A mixture of the material so obtained, 10% palladium-on-carbon (0.095 g) and methanol (20 ml) was stirred under an atmosphere of hydrogen gas. After cessation of hydrogen uptake, the catalyst was removed by filtration and the filtrate was evaporated. There was thus obtained the required starting material (0.18 g); NMR Spectrum: (DMSOd$_6$) 1.0 (t, 3H), 2.28–2.36 (m, 2H), 2.38–2.41 (m, 4H), 3.15–3.21 (m, 4H), 4.5 (broad s, 2H), 6.58 (d, 1H), 6.85 (d, 1H), 7.57 (s, 1H); Mass Spectrum: M+H$^+$ 207.

EXAMPLE 5

Using an analogous procedure to that described in Example 4, the appropriate 5-aminopyridine was reacted with 2-chloro-5-(2-morpholinopyrid-4-ylcarbonylamino) benzoic acid to give the compounds described in Table II.

TABLE II

| No. | R$^1$ | R$^3$ | Note |
|---|---|---|---|
| 1 | N-(2-dimethylaminoethyl)-N-methylamino | chloro | a |
| 2 | N-(3-dimethylaminopropyl)-N-methylamino | chloro | b |
| 3 | 4-methylpiperazin-1-yl | chloro | c |
| 4 | 4-methylhomopiperazin-1-yl | chloro | d |

Notes
a) The product gave the following data: NMRSpectrum: (DMSOd$_6$) 2.4–2.49(m, 8H), 2.98(s, 3H), 3.48–3.53(m, 4H), 3.66–3.72(m, 6H), 6.61 (m, 1H), 7.1(d, 1H), 7.23(s, 1H), 7.53(d, 1H), 7.78–7.82(m, 1H), 7.88–7.93(m, 2H), 8.27–8.38(m, 2H), 10.26(s, 1H), 10.51(s, 1H); MassSpectrum: M + H$^+$ 538 and 540.

The 5-amino-2-[N-(2-dimethylaminoethyl)-N-methylamino]pyridine used as a starting material was prepared from 2-chloro-5-nitropyridine and N-(2-dimethylaminoethyl)-N-methylamine using analogous procedures to those described in the portion of Example 4 which is concerned with the preparation of 5-amino-2-(4-ethylpiperazin-1-yl)pyridine. The required starting material gave the following data: NMR Spectrum: (DMSOd$_6$) 2.35 (t, 2H), 2.48 (s, 6H), 2.82 (s, 3H), 3.32–3.44 (m, 6H), 6.4 (m, 1H), 6.84–6.9 (m, 1H), 7.53–7.56 (m, 1H); Mass Spectrum: M+H$^+$ 195.

b) The product was purified by column chromatography on an isolute SCX ion exchange column using initially methanol and then a 99:1 mixture of methanol and a saturated aqueous ammonium hydroxide solution as eluent. The product gave the following data: Mass Spectrum: M+H$^+$ 552 and 554.

The 5-amino-2-[N-(3-dimethylaminopropyl)-N-methylamino]pyridine used as a starting material was prepared from 2-chloro-5-nitropyridine and N-(3-dimethylaminopropyl)-N-methylamine using analogous procedures to those described in the portion of Example 4 which is concerned with the preparation of 5-amino-2-(4-ethylpiperazin-1-yl)pyridine. The required starting material gave the following data: NMR Spectrum: (DMSOd$_6$) 1.48–56 (m, 2H), 2.08 (s, 6H), 2.16 (t, 2H), 2.49 (s, 3H), 3.29–3.36 (m, 2H), 4.28 (broad s, 2H), 6.37–6.42 (m, 1H), 6.84–6.9 (m, 1H), 7.53 (s, 1H); Mass Spectrum: M+H$^+$ 209.

c) The product gave the following data: NMR Spectrum: (DMSOd$_6$) 2.19 (s, 3H), 2.36–2.39 (m, 4H), 3.39–3.43 (m, 4H), 3.39–3.52 (m, 4H), 3.68–3.71 (m, 4H), 6.84 (d, 1H), 7.08 (d, 1H), 7.23 (s, 1H), 7.52 (d, 1H), 7.84–7.94 (m, 3H), 8.27 (d, 1H), 8.39 (s, 1H); Mass Spectrum: M+H$^+$ 536 and 538.

The 5-amino-2-(4-methylpiperazin-1-yl)pyridine used as a starting material was prepared from 2-chloro-5-nitropyridine and N-methylpiperazine using analogous procedures to those described in the portion of Example 4 which is concerned with the preparation of 5-amino-2-(4-ethylpiperazin-1-yl)pyridine. The required starting material gave the following data: NMR Spectrum: (DMSOd$_6$) 2.26 (s, 3H), 2.47–2.49 (m, 4H), 3.21–3.25 (m, 4H), 6.6 (d, 1H), 6.9 (d, 1H), 7.57 (s, 1 H); Mass Spectrum: M+H$^+$ 193.

d) The product was purified by column chromatography on an isolute SCX ion exchange column using initially methanol and then a 99:1 mixture of methanol and a saturated aqueous ammonium hydroxide solution as eluent. The product gave the following data: Mass Spectrum: M+H$^+$ 550 and 552.

The 5-amino-2-(4-methylhomopiperazin-1-yl)pyridine used as a starting material was prepared from 2-chloro-5-nitropyridine and N-methylhomopiperazine using analogous procedures to those described in the portion of Example 4 which is concerned with the preparation of 5-amino-2-(4-ethylpiperazin-1-yl)pyridine. The required starting material gave the following data: Mass Spectrum: M+H$^+$ 207.

EXAMPLE 6

N-[3-(4-methylpiperazin-1-ylmethyl)phenyl]-2-chloro-5-(2-morpholinopyrid-4-ylcarbonylamino)benzamide Using an analogous procedure to that described in Example 4, 3-(4-methylpiperazin-1-ylmethyl)aniline was reacted with 2-chloro-5-(2-morpholinopyrid-4-ylcarbonylamino)benzoic acid to give the title compound in 32% yield; NMR Spectrum: (DMSOd$_6$) 2.13 (s, 3H), 2.31–2.35 (m, 8H), 3.42 (s, 2H), 3.49–3.53 (m, 4H), 3.69–3.72 (m, 4H), 7.02 (d, 1H), 7.1 (d, 1H), 7.22–7.3 (m, 2H), 7.57–7.65 (m, 3H), 7.84–7.94 (m, 2H), 8.28 (d, 1H), 10.47 (s, 1H), 10.52 (s, 1H); Mass Spectrum: M+H$^+$ 549 and 551.

EXAMPLE 7

Pharmaceutical Compositions

The following illustrate representative pharmaceutical dosage forms of the invention as defined herein (the active ingredient being termed "Compound X"), for therapeutic or prophylactic use in humans:

| (a) | Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |

| (b) | Tablet II | mg/tablet |
|---|---|---|
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |

| (c) | Tablet III | mg/tablet |
|---|---|---|
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |

| (d) | Capsule | mg/capsule |
|---|---|---|
| | Compound X | 10 |
| | Lactose Ph.Eur | 488.5 |
| | Magnesium | 1.5 |

| (e) | Injection I | (50 mg/ml) |
|---|---|---|
| | Compound X | 5.0% w/v |
| | 1 M Sodium hydroxide solution | 15.0% v/v |
| | 0.1 M Hydrochloric acid (to adjust pH to 7.6) | 4.5% w/v |
| | Polyethylene glycol 400 | |
| | Water for injection to 100% | |

| (f) | Injection II | (10 mg/ml) |
|---|---|---|
| | Compound X | 1.0% w/v |
| | Sodium phosphate BP | 3.6% w/v |
| | 0.1 M Sodium hydroxide solution | 15.0% v/v |
| | Water for injection to 100% | |

| (g) | Injection III | (1 mg/ml, buffered to pH 6) |
|---|---|---|
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

| (h) | Aerosol I | mg/ml |
|---|---|---|
| | Compound X | 10.0 |
| | Sorbitan trioleate | 13.5 |
| | Trichlorofluoromethane | 910.0 |
| | Dichlorodifluoromethane | 490.0 |

| (i) | Aerosol II | mg/ml |
|---|---|---|
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

| (j) | Aerosol III | mg/ml |
|---|---|---|
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |

| (k) | Aerosol IV | mg/ml |
|---|---|---|
| | Compound X | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |

| (l) | Ointment | ml |
|---|---|---|
| | Compound X | 40 mg |
| | Ethanol | 300 μl |
| | Water | 300 μl |

-continued

| | | |
|---|---|---|
| | 1-Dodecylazacycloheptan-2-one | 50 μl |
| | Propylene glycol | to 1 ml |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. A compound of the Formula I

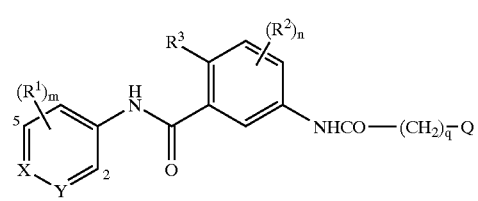

wherein

X and Y are both CH, or

X and Y are both N;

m is 0, 1, 2 or 3;

$R^1$ is hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)

alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino or di-[(1–6C)alkyl]amino-(2–6C)alkanoylamino, or R¹ is aryl, aryl-(1–6C)alkyl, aryl-(1–6C)alkoxy, aryloxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-1-(1–6C)alkylamino, heteroarylcarbonylamino, heteroarylsulphonylamino, N-heteroarylsulphamoyl, heteroaryl-(2–6C)alkanoylamino, heteroaryl-(1–6C)alkoxy-(1–6C)alkyl, heteroaryl-(1–6C)alkylamino-(1–6C)alkyl, N-(1–6C)alkyl-heteroaryl-(1–6C)alkylamino-(1–6C)alkyl, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl, heterocyclyl-(2–6C)alkanoylamino, heterocyclyl-(1–6C)alkoxy-(1–6C)alkyl, heterocyclyl-(1–6C)alkylamino-(1–6C)alkyl or N-(1–6C)alkyl-heterocyclyl-(1–6C)alkylamino-(1–6C)alkyl, or (R¹)ₘ is a (1–3C)alkylenedioxy group, and wherein any of the R¹ substituents defined hereinbefore which comprises a CH₂ group which is attached to 2 carbon atoms or a CH₃ group which is attached to a carbon atom may optionally bear on each said CH₂ or CH₃ group a substituent selected from hydroxy, amino, (1–6C)alkoxy, (1–6C)alkylamino, di-[(1–6C)alkyl]amino and heterocyclyl, and wherein any aryl, heteroaryl or heterocyclyl group in a R¹ substituent may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl]carbamoyl, (2–6C)alkanoyl, amino, (1–6C)alkylamino, di-[(1–6C)alkyl]amino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl, n is 0, 1, 2 or 3;

R² hydroxy, halogeno, trifluoromethyl, cyano, mercapto, nitro, amino, carboxy, (1–6C)alkoxycarbonyl, (1–6C)alkyl, (2–6C)alkenyl, (2–6C)alkynyl, (1–6C)alkoxy, (1–6C)alkylamino or di-[(1–6C)alkyl]amino;

R³ is hydrogen, halogeno, (1–6C)alkyl or (1–6C)alkoxy;

q is 0, 1, 2, 3 or 4; and

Q is aryl, aryloxy, aryl-(1–6C)alkoxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylcarbonyl, N-arylsulphamoyl, aryl-(2–6C)alkanoylamino, (3–7C)cycloalkyl, heteroaryl, heteroaryloxy, heteroaryl-(1–6C)alkoxy, heteroarylamino, N-(1–6C)alkyl-heteroarylamino, heteroaryl-(1–6C)alkylamino, N-(1–6)alkyl-heteroaryl-(1–6C)alkylamino, heteroarylcarbonylamino, heteroarylsulphonylamino, N-heteroarylcarbamoyl, N-heteroarylsulphamoyl, heteroaryl-(2–6C)alkanoylamino, heterocyclyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylcarbamoyl, N-heterocyclylsulphamoyl or heterocyclyl-(2–6C)alkanoylamino, and Q is optionally substituted with 1, 2 or 3 substituents selected from hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)

alkylamino, N-(1–6C)alkyl-N,N-di-[(1–6C)alkyl]
carbamoyl-(1–6C)alkylamino, N-(1–6C)alkyl-amino-
(2–6C)alkylamino, N-(1–6C)alkyl-(1–6C)alkylamino-
(2–6C)alkylamino, N-(1–6C)alkyl-di-[(1–6C)alkyl]
amino-(2–6C)alkylamino, halogeno-(2–6C)
alkanoylamino, hydroxy-(2–6C)alkanoylamino,
(1–6C)alkoxy-(2–6C)alkanoylamino, cyano-(2–6C)
alkanoylamino, carboxy-(2–6C)alkanoylamino,
(1–6C)alkoxycarbonyl-(2–6C)alkanoylamino,
carbamoyl-(2–6C)alkanoylamino, N-(1–6C)
alkylcarbamoyl-(2–6C)alkanoylamino, N,N-di-
[(1–6C)alkyl]carbamoyl-(2–6C)alkanoylamino,
amino-(2–6C)alkanoylamino, (1–6C)alkylamino-
(2–6C)alkanoylamino, di-[(1–6C)alkyl]amino-(2–6C)
alkanoylamino, aryl, aryl-(1–6C)alkyl, aryl-(1–6C)
alkoxy, aryloxy, arylamino, N-(1–6C)alkyl-arylamino,
aryl-(1–6C)alkylamino, N-(1–6C)alkyl-aryl-(1–6C)
alkylamino, aroylamino, arylsulphonylamino,
N-arylsulphamoyl, aryl-(2–6C)alkanoylamino,
heteroaryl, heteroaryl-(1–6C)alkyl, heteroaryloxy,
heteroaryl-(1–6C)alkoxy, heteroarylamino, N-(1–6C)
alkyl-heteroarylamino, heteroaryl-(1–6C)alkylamino,
N-(1–6C)alkyl-heteroaryl-(1–6C)alkylamino,
heteroarylcarbonylamino, heteroarylsulphonylamino,
N-heteroarylsulphamoyl, heteroaryl-(2–6C)
alkanoylamino, heteroaryl-(1–6C)alkoxy-(1–6C)alkyl,
heteroaryl-(1–6C)alkylamino-(1–6C)alkyl, N-(1–6C)
alkyl-heteroaryl-(1–6C)alkylamino-(1–6C)alkyl,
heterocyclyl, heterocyclyl-(1–6C)alkyl,
heterocyclyloxy, heterocyclyl-(1–6C)alkoxy,
heterocyclylamino, N-(1–6C)alkyl-heterocyclylamino,
heterocyclyl-(1–6C)alkylamino, N-(1–6C)alkyl-
heterocyclyl-(1–6C)alkylamino,
heterocyclylcarbonylamino,
heterocyclylsulphonylamino,
N-heterocyclylsulphamoyl, heterocyclyl-(2–6C)
alkanoylamino, heterocyclyl-(1–6C)alkoxy-(1–6C)
alkyl, heterocyclyl-(1–6C)alkylamino-(1–6C)alkyl and
N-(1–6C)alkyl-heterocyclyl-(1–6C)alkylamino-(1–6C)
alkyl, or Q is substituted with a (1–3C)alkylenedioxy
group, and wherein any of the substituents on Q defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino, di-[(1–6C)alkyl]amino and heterocyclyl, and wherein any aryl, heteroaryl or heterocyclyl group in a substituent on Q may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl] carbamoyl, (2–6C)alkanoyl, amino, (1–6C)alkylamino, di-[(1–6C)alkyl]amino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C) alkylamino-(1–6C)alkyl, di-[(1–6C)alkyl]amino-(1–6C)alkyl, aryl and aryl-(1–6C)alkyl;

or a pharmaceutically-acceptable salt or in-vivo-cleavable ester thereof.

2. A compound of the Formula I according to claim 1 wherein $R^3$ is selected from halogeno and (1–6C)alkyl; or a pharmaceutically-acceptable salt or in-vivo-cleavable ester thereof.

3. A compound of the Formula I according to claim 1 wherein

X and Y are CH, or

X and Y are both N;

$R^3$ is hydrogen, fluoro, chloro, bromo, methyl or ethyl;

m is 0, 1 or 2;

$R^1$ is hydroxy, fluoro, chloro, bromo, trifluoromethyl, cyano, methyl, ethyl, propyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-(2-dimethylaminoethyl)-N-methylamino, N-(2-diethylaminoethyl)-N-methylamino, N-(3-dimethylaminopropyl)-N-methylamino, N-(3-diethylaminopropyl)-N-methylamino, pyridyl, pyridylmethyl, pyridylmethoxy, pyrrolidinyl, piperidinyl, morpholinyl, piperazinyl, 4-methylpiperazinyl, homopiperazinyl, 4-methylhomopiperazinyl, 4-acetylpiperazinyl, pyrrolidinylmethyl, piperidinylmethyl, morpholinylmethyl, piperazinylmethyl, 4-methylpiperazinylmethyl, 4-acetylpiperazinylmethyl, pyrrolidinyloxy, 1-methylpyrrolidinyloxy, piperidinyloxy, 1-methylpiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl) ethoxy, 3-(4-methylpiperazinyl)propoxy, 2-(4-acetylpiperazinyl)ethoxy or 3-(4-acetylpiperazinyl) propoxy;

n is 0 or 1;

$R^2$ is fluoro, chloro, bromo, methyl or ethyl;

q is 0; and

Q is phenyl, furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, pyridyl, pyridylmethyl, pyridylmethoxy, pyrrolidinyl, piperidinyl, morpholinyl, piperazinyl, 4-methylpiperazinyl, homopiperazinyl, 4-methylhomopiperazinyl, 4-acetylpiperazinyl, pyrrolidinylmethyl, piperidinylmethyl, morpholinylmethyl, piperazinylmethyl, 4-methylpiperazinylmethyl, 4-acetylpiperazinylmethyl, pyrrolidinyloxy, 1-methylpyrrolidinyloxy, piperidinyloxy, 1-methylpiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy and 3-(4-acetylpiperazinyl)propoxy;

or a pharmaceutically-acceptable salt thereof.

4. A compound of the Formula I according to claim 1 wherein

X is CH;

Y is CH;

$R^3$ is hydrogen, chloro or methyl;

m is 0, 1 or 2;

$R^1$ is hydroxy, fluoro, chloro, bromo, trifluoromethyl, cyano, methyl, ethyl, propyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-(2-dimethylaminoethyl)-N-methylamino, N-(2-diethylaminoethyl)-N-methylamino, N-(3-dimethylaminopropyl)-N-methylamino, N-(3-diethylaminopropyl)-N-methylamino, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy or 3-(4-acetylpiperazin-1-yl)propoxy;

n is 0;

q is 0; and

Q is phenyl, 2-pyridyl, 3-pyridyl or 4-pyridyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridyl, 3-pyridyl, 4-pyridyl, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy;

or a pharmaceutically-acceptable salt thereof.

5. A compound of the Formula I according to claim 1 wherein

X is CH;

Y is CH;

$R^3$ is hydrogen, chloro or methyl;

m is 1;

$R^1$ is selected from diethylaminomethyl, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, homopiperazin-1-yl, 4-methylhomopiperazin-1-yl, piperazin-1-ylmethyl, 4-methylpiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, pyrrolidin-3-yloxy, piperidin-4-yloxy, 2-pyrrolidin-1-ylethoxy, 2-piperidinoethoxy, 2-morpholinoethoxy, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl and 2-pyridylmethoxy;

n is 0;

q is 0; and

Q is 3-pyridyl or 4-pyridyl which bears a substituent selected from pyrrolidin-1-yl, morpholino, piperidino, piperazin-1-yl and 4-methylpiperazin-1-yl;

or a pharmaceutically-acceptable salt thereof.

6. A compound of the Formula I according to claim 1 wherein

X is CH;

Y is CH;

$R^3$ is hydrogen, chloro or methyl;

m is 1;

$R^1$ is N-(3-dimethylaminopropyl)-N-methylamino, 4-methylpiperazin-1-yl, 4-methylhomopiperazin-1-yl, 4-methylpiperazin-1-ylmethyl or pyrrolidin-3-yloxy;

n is 0;

q is 0; and

Q is 2-morpholinopyrid-4-yl;

or a pharmaceutically-acceptable salt thereof.

7. A compound of the Formula I according to claim 1 wherein

X and Y are both CH, or

X and Y are both N;

$R^3$ is fluoro, chloro, bromo, methyl or ethyl;

m is 0, 1 or 2;

$R^1$ is hydroxy, fluoro, chloro, bromo, trifluoromethyl, cyano, methyl, ethyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3-ethylaminopropyl)-N-methylamino, N-2-dimethylaminoethyl)-N-methylamino, N-(2-diethylaminoethyl)-N-methylamino, N-(3-dimethylaminopropyl)-N-methylamino, N-(3-diethylaminopropyl)-N-methylamino, pyridyl, pyridylmethyl, pyridylmethoxy, 3-pyrrolinyl, pyrrolidinyl, piperidinyl, homopiperidinyl, morpholinyl, piperazinyl, 4-methylpiperazinyl, 4-ethylpiperazinyl, homopiperazinyl, 4-methylhomopiperazinyl, 4-acetylpiperazinyl, pyrrolidinylmethyl, piperidinylmethyl, morpholinylmethyl, piperazinylmethyl, 4-methylpiperazinylmethyl, homopiperazinylmethyl, 4-methylhomopiperazinylmethyl, 4-acetylpiperazinylmethyl, pyrrolidinyloxy, 1-methylpyrrolidinyloxy, piperidinyloxy, 1-methylpiperidinyloxy, homopiperidinyloxy, 1-methylhomopiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy, 3-(4-acetylpiperazinyl)propoxy, 3-dimethylaminopropylaminomethyl, 3-dimethylamino-2,2-dimethylpropylaminomethyl, 2-(1-methylpyrrolidinylethyl)aminomethyl, 3-pyrrolidinylpropylaminomethyl, 2-morpholinylethylaminomethyl, 3-morpholinylpropylaminomethyl, 2-piperazinylethylaminomethyl, 3-(4-methylpiperazinylpropyl)aminomethyl, pyridylmethoxy, imidazolylmethoxy, thiazolylmethoxy and 2-methylthiazolylmethoxy;

n is 0 or 1;

$R^2$ is fluoro, chloro, bromo, methyl or ethyl;

q is 0; and

Q is phenyl, indenyl, indanyl, tetrahydronaphthyl, fluorenyl, furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl which optionally bears 1 or 2 substituents selected from hydroxy, fluoro, chloro, trifluoromethyl, cyano, amino, methyl, ethyl, methoxy, ethoxy, propoxy, isopropoxy, cyclopentyloxy, methylenedioxy, methylamino, ethylamino, dimethylamino, diethylamino, acetamido, propionamido, methanesulphonamido, N-methylmethanesulphonamido, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, phenyl, furyl, thienyl, pyridyl, pyridylmethyl, pyridylmethoxy, azetidinyl, 3-pyrrolinyl, pyrrolidinyl, piperidinyl, homopiperidinyl, morpholinyl, piperazinyl, 4-methylpiperazinyl, homopiperazinyl, 4-methylhomopiperazinyl, 4-acetylpiperazinyl, pyrrolidinylmethyl, piperidinylmethyl, morpholinylmethyl, piperazinylmethyl, 4-methylpiperazinylmethyl, 4-acetylpiperazinylmethyl, pyrrolidinyloxy, 1-methylpyrrolidinyloxy, piperidinyloxy, 1-methylpiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy and 3-(4-acetylpiperazinyl)propoxy, and wherein any phenyl, furyl, thienyl, pyridyl or heterocyclyl group in a substituent on Q may optionally bear 1 or 2 substituents selected from fluoro, chloro, methyl and methoxy;

or a pharmaceutically-acceptable salt thereof.

8. A compound of the Formula I according to claim 1 wherein

X is CH;

Y is CH;

$R^3$ is chloro or methyl;

m is 0, 1 or 2;

$R^1$ is hydroxy, fluoro, chloro, bromo, trifluoromethyl, cyano, methyl, ethyl, propyl, methoxy, ethoxy, amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-methylaminoethylamino, 2-ethylaminoethylamino, 3-methylaminopropylamino, 3-ethylaminopropylamino, 2-dimethylaminoethylamino, 2-diethylaminoethylamino, 3-dimethylaminopropylamino, 3-diethylaminopropylamino, N-(2-aminoethyl)-N-methylamino, N-(3-aminopropyl)-N-methylamino, N-(2-methylaminoethyl)-N-methylamino, N-(2-ethylaminoethyl)-N-methylamino, N-(3-methylaminopropyl)-N-methylamino, N-(3)-ethylaminopropyl)-N-methylamino, N-(2-dimethylaminoethyl)-N-methylamino, N-(2-diethylaminoethyl)-N-methylamino, N-(3-dimethylaminopropyl)-N-methylamino, N-(3-diethylaminopropyl)-N-methylamino, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidine-4-yloxy, 1-methylpiperidin-4-yloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy or 3-(4-acetylpiperazin-1-yl)propoxy;

n is 0;

q is 0; and

Q is phenyl, 2-pyridyl, 3-pyridyl or 4-pyridyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridyl, 3-pyridyl, 4-pyridyl, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, homopiperazin-1-yl, 4-methylhomopiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, pyrrolidin-3-yloxy, 1-methylpyrrolidin-3-yloxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy;

or a pharmaceutically-acceptable salt thereof.

9. A compound of the Formula I according to claim 1 wherein

X is CH;

Y is CH;

$R^3$ is chloro or methyl;

m is 1 or 2;

$R^1$ is hydroxy, fluoro, chloro, methyl, ethyl, propyl, methoxy, dimethylaminomethyl, diethylaminomethyl, 2-dimethylaminoethoxy, 2-diethylaminoethoxy, 3-dimethylaminopropoxy, 3-diethylaminopropoxy, 3-dimethylamino-2-hydroxypropoxy, 3-diethylamino-2-hydroxypropoxy, 2-aminoethylamino, 3-aminopropylamino, 4-aminobutylamino, 3-methylaminopropylamino, 2-dimethylaminoethylamino, 2-diethylaminoethylamino, 3-dimethylaminopropylamino, 4-dimethylaminobutylamino, 3-amino-2-hydroxypropylamino, 3-dimethylamino-2-hydroxypropylamino, N-(2-dimethylaminoethyl)-N-methylamino, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, 4-(2-hydroxyethyl)piperazin-1-yl, homopiperazin-1-yl, 4-methylhomopiperazin-1-yl, piperazin-1-ylmethyl, 4-methylpiperazin-1-ylmethyl, homopiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, 4-(2-hydroxyethyl)piperazin-1-ylmethyl, pyrrolidin-3-yloxy, 1-methylpyrrolidin-3-yloxy, piperidin-4-yloxy, 1-methylpiperidin-4-yloxy, 1-benzylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-hydroxy-3-pyrrolidin-1-ylpropoxy, 2-hydroxy-3-piperidinopropoxy, 2-hydroxy-3- morpholinopropoxy, piperidin-4-ylamino, 1-methylpiperidin-4-ylamino, 1-benzylpiperidin-4-ylamino, 2-pyrrolidin-1-ylethylamino, 3-pyrrolidin-1ylpropylamino, 2-morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino, 3-(4-methylpiperazin-1-yl)propylamino, 2-(1-methylpyrrolidin-2-yl)ethylamino, 3-(1-methylpyrrolidin-2-yl)propylamino, 2-dimethylaminoethylaminomethyl, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl or 2-pyridylmethoxy;

n is 0;

q is 0; and

Q is 2-pyridyl, 3-pyridyl or 4-pyridyl which bears a substituent selected from pyrrolidin-1-yl, 3-hydroxypyrrolidin-1-yl, 2-hydroxymethylpyrrolidin-1-yl, morpholino, piperidino, 4-hydroxypiperidin-1-yl, piperazin-1-yl, and 4-methylpiperazin-1-yl;

or a pharmaceutically-acceptable salt thereof.

10. A compound of the Formula I according to claim 1 wherein

X is CH;

Y is CH;

R$^3$ is chloro or methyl;

m is 1;

R$^1$ is selected from diethylaminomethyl, N-(2-dimethylaminoethyl)-N-methylamino, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, homopiperazin-1-yl, 4-methylhomopiperazin-1-yl, piperazin-1-ylmethyl, 4-methylpiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, pyrrolidin-3-yloxy, piperidin-4-yloxy, 2-pyrrolidin-1-ylethoxy, 2-piperidinoethoxy, 2-morpholinoethoxy, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl and 2-pyridylmethoxy;

n is 0;

q is 0; and

Q is 3-pyridyl or 4-pyridyl which bears a substituent selected from pyrrolidin-1-yl, morpholino, piperidino, piperazin-1-yl and 4-methylpiperazin-1-yl;

or a pharmaceutically-acceptable salt thereof.

11. A compound of the Formula I according to claim 1 wherein

X is CH;

Y is CH;

R$^3$ is chloro or methyl;

m is 1;

R$^1$ is selected from diethylaminomethyl, N-(2-dimethylaminoethyl)-N-methylamino, N-(3-dimethylaminopropyl)-N-methylamino, 3-pyrrolidin-1-yl, pyrrolidin-1-yl, morpholino, piperidino, homopiperidin-1-yl, piperazin-1-yl, 4-methylpiperazin-1-yl, 4-ethylpiperazin-1-yl, homopiperazin-1-yl, 4-methylhomopiperazin-1-yl, piperazin-1-ylmethyl, 4-methylpiperazin-1-ylmethyl, homopiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, pyrrolidin-3-yloxy, N-methylpyrrolidin-3-yloxy, piperidin-4-yloxy, N-methylpiperidin-4-yloxy, homopiperidin-4-yloxy, N-methylhomopiperidin-4-yloxy, 2-pyrrolidin-1-ylethoxy, 2-piperidinoethoxy, 2-morpholinoethoxy, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl, 2-pyridylmethoxy, 4-thiazolylmethoxy and 2-methylthiazol-4-ylmethoxy;

n is 0;

q is 0; and

Q is phenyl which bears 1 or 2 substituents selected from fluoro, chloro, trifluoromethyl, methoxy, cyclopentyloxy, acetamido, N-methylmethanesulphonamido, 2-furyl, azetidin-1-yl, 3-pyrrolidin-1-yl, pyrrolidin-1-yl, morpholino, piperidino, homopiperidino, piperazin-1-yl, homopiperazin-1-yl, 4-methylpiperazin-1-yl, and 4-methylhomopiperazin-1-yl, or Q is 1-fluorenyl or 4-dibenzofuranyl, or Q is 3-pyridyl or 4-pyridyl which bears a substituent selected from azetidin-1-yl, 3-pyrrolidin-1-yl, pyrrolidin-1-yl, morpholino, piperidino, homopiperidino, piperazin-1-yl, homopiperazin-1-yl, 4-methylpiperazin-1-yl and 4-methylhomopiperazin-1-yl;

or a pharmaceutically-acceptable salt thereof.

12. A compound of the Formula I according to claim 1 wherein

X is CH;

Y is CH;

R$^3$ is chloro or methyl;

m is 1;

R$^1$ is N-(2-dimethylaminoethyl)-N-methylamino, N-(3-dimethylaminopropyl)-N-methylamino, 4-methylpiperazin-1-yl, 4-ethylpiperazin-1-yl, 4-methylhomopiperazin-1-yl or 4-methylpiperazin-1-ylmethyl;

n is 0;

q is 0; and

Q is 2-(pyrrolidin-1-yl)pyrid-4-yl, 2-(3-pyrrolin-1-yl)pyrid-4-yl, 2-piperidinopyrid-4-yl, 2-morpholinopyrid-4-yl, 1-fluorenyl, dibenzofuran-4-yl, 3-acetamidophenyl or 3-(2-furyl)phenyl;

or a pharmaceutically-acceptable salt thereof.

13. A compound of the Formula I according to claim 1 wherein

X is CH;
Y is CH;
R³ is chloro or methyl;
m is 1;
R¹ is N-(3-dimethylaminopropyl)-N-methylamino, 4-methylpiperazin-1-yl, 4-methylhomopiperazin-1-yl or 4-methylpiperazin-1-ylmethyl;
n is 0;
q is 0; and
Q is 2-morpholinopyrid-4-yl;
or a pharmaceutically-acceptable salt thereof.

14. A compound of the Formula I according to claim 1 which is:

N-[3-(4-methylpiperazin-1-ylmethyl)phenyl]-2-methyl-5-(2-morpholinopyrid-4-ylcarbonylamino)benzamide,
or a pharmaceutically-acceptable salt thereof.

15. A process for the preparation of A compound of the Formula I, or a pharmaceutically-acceptable salt or in-vivo-cleavable ester thereof, according to claim 1 which comprises:

(a) reacting an aniline of the Formula II

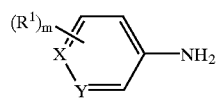

II with a benzoic acid of the Formula III, or an activated derivative thereof,

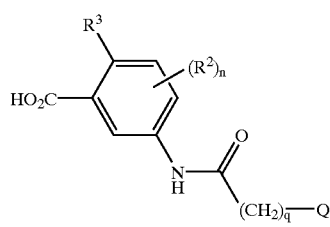

III under standard amide bond forming conditions, wherein variable groups are as defined in claim 1 and wherein any functional group is protected, if necessary, and:
(i) removing any protecting groups;
(ii) optionally forming a pharmaceutically-acceptable salt or in-vivo-cleavable ester;

(b) reacting an aniline of the Formula VI

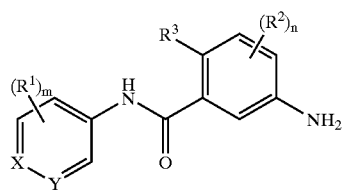

VI with a carboxylic acid of the Formula V, or a reactive derivative thereof,

HO₂C—(CH₂)$_q$—Q  V under standard amide bond forming conditions, wherein variable groups are as defined in claim 1 and wherein any functional group is protected if necessary, and:
(i) removing any protecting groups; and
(ii) optionally forming a pharmaceutically-acceptable salt or in-vivo-cleavable ester;

(c) an amide derivative of the Formula I wherein R¹ or a substituent on Q is (1–6C)alkoxy or substituted (1–6C)alkoxy, (1–6C)alkylthio, (1–6C)alkylamino, di-[(1–6C)alkyl]amino or substituted (1–6C)alkylamino may be prepared by the alkylation, conveniently in the presence of a suitable base, of an amide derivative of the Formula I wherein R¹ or a substituent on Q is hydroxy, mercapto or amino as appropriate;

(d) an amide derivative of the Formula I wherein a substituent on Q is amino, (1–6C)alkylamino, di-[(1–6C)alkyl]amino, substituted (1–6C)alkylamino, substituted N-(1–6C)alkyl-(2–6C)alkylamino or a N-linked heterocyclyl group may be prepared by the reaction, conveniently in the presence of a suitable base, of an amide derivative of the Formula I wherein a substituent on Q is a suitable leaving group with an appropriate amine;

(e) an amide derivative of the Formula I wherein R¹ or a substituent on Q is (1–6C)alkanoylamino or substituted (2–6C)alkanoylamino may be prepared by the acylation of a compound of the Formula I wherein R¹ or a substituent on Q is amino;

(f) an amide derivative of the Formula I wherein R¹ or a substituent on Q is (1–6C)alkanesulphonylamino may be prepared by the reaction of a compound of the Formula I wherein R¹ or a substituent on Q is amino with a (1–6C)alkanesulphonic acid, or an activated derivative thereof;

(g) an amide derivative of the Formula I wherein R¹ or a substituent on Q is carboxy, carboxy-(1–6C)alkyl, carboxy-(1–6C)alkoxy, carboxyl-(1–6C)alkylamino, N-(1–6C)alkyl-carboxy-(1–6C)alkylamino or carboxy-(2–6C)alkanoylamino may be prepared by the cleavage of a compound of the Formula I wherein R¹ or a substituent on Q is (1–6C)alkoxycarbonyl, (1–6C)alkoxycarbonyl-(1–6C)alkyl, (1–6C)alkoxycarbonyl-(1–6C)alkoxy, (1–6C)alkoxycarbonyl-(1–6C)alkylamino, N-(1–6C)alkyl-(1–6C)alkoxycarbonyl-(1–6C)alkylamino or (1–6C)alkoxycarbonyl-(2–6C)alkanoylamino as appropriate; or (h) an amide derivative of the Formula I wherein R¹ is amino-(1–6C)alkyl, (1–6C)alkylamino-(1–6C)alkyl, di-[(1–6C)alkyl]amino-(1–6C)alkyl or a heterocyclyl-(1–6C)alkyl group may be prepared by the reaction, conveniently in the presence of a suitable base, of a compound of the Formula IX

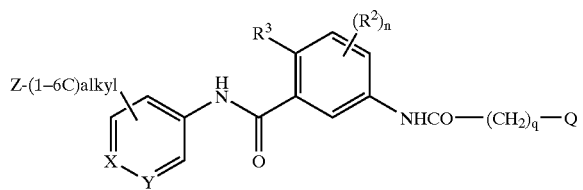

wherein X, Y, R², R³, n, q and Q have any of the meanings defined in claim 1 and Z is a suitable leaving group with an appropriate amine or heterocycle.

16. A pharmaceutical composition which comprises a compound of the Formula I, or a pharmaceutically-acceptable or in-vivo-cleavable ester thereof, according to claim 1 in association with a pharmaceutically-acceptable diluent or carrier.

17. A method of treating a disease or medical conditions mediated by the production or effect of cytokines, which method comprises administering to a warm-blooded animal in need thereof a cytokine inhibiting amount of a compound of the Formula I, or a pharmaceutically-acceptable salt or in-vivo-cleavable ester thereof, according to claim 1.

* * * * *